United States Patent [19]
Foos et al.

[11] Patent Number: 5,518,601
[45] Date of Patent: May 21, 1996

[54] EXTENDED USE PLANAR SENSORS

[75] Inventors: Joseph S. Foos, Needham; Peter G. Edelman, Franklin; James E. Flaherty, Attleboro, all of Mass.; Joseph Berger, Basel, Switzerland

[73] Assignee: Ciba Corning Diagnostics Corp., Medfield, Mass.

[21] Appl. No.: 492,428

[22] Filed: Aug. 24, 1995

Related U.S. Application Data

[62] Division of Ser. No. 209,081, Mar. 9, 1994, which is a division of Ser. No. 45,847, Apr. 9, 1993, Pat. No. 5,387,329.

[51] Int. Cl.[6] .......................... G01N 27/26; B23P 19/00; H01R 43/00
[52] U.S. Cl. .......................... 204/415; 204/400; 204/401; 204/406; 29/729; 29/738; 29/745; 29/746; 29/825; 205/782.5; 205/791; 205/791.5
[58] Field of Search .................... 204/400, 401, 204/415, 403, 153.17, 153.1, 406; 29/825, 829, 846, 857, 874, 729, 738, 745, 746, 876

[56] References Cited

U.S. PATENT DOCUMENTS

| | | | |
|---|---|---|---|
| 3,260,656 | 7/1966 | Ross | 204/1 |
| 3,714,015 | 1/1973 | Niedrach | 204/416 |
| 3,719,564 | 3/1973 | Lilly et al. | 204/1 |
| 3,776,832 | 12/1973 | Oswin et al. | 204/195 |
| 4,076,596 | 2/1978 | Connery et al. | 204/1 |
| 4,100,048 | 7/1978 | Pompei et al. | 204/195 |
| 4,158,736 | 6/1979 | Lewis et al. | 560/205 |
| 4,172,770 | 10/1979 | Sermersky et al. | 204/1 |
| 4,214,968 | 7/1980 | Battaglia et al. | 204/418 |
| 4,225,410 | 9/1980 | Pace | 204/403 |
| 4,324,257 | 4/1982 | Albarda et al. | 128/635 |
| 4,450,842 | 5/1984 | Zick et al. | 128/635 |
| 4,534,356 | 8/1985 | Papadakis et al. | 204/403 |
| 4,536,274 | 9/1985 | Papadakis et al. | 204/415 |

(List continued on next page.)

FOREIGN PATENT DOCUMENTS

| | | |
|---|---|---|
| 0097554 | 4/1984 | European Pat. Off. . |
| 0267892 | 5/1988 | European Pat. Off. . |
| 0311377 | 4/1989 | European Pat. Off. . |
| 0351516 | 1/1990 | European Pat. Off. . |
| 0473541 | 8/1991 | European Pat. Off. . |
| 0494382 | 12/1991 | European Pat. Off. . |
| 3195964 | 8/1991 | Japan . |
| 2073891 | 10/1981 | United Kingdom . |
| 8808975 | 11/1988 | WIPO . |
| 8907263 | 8/1989 | WIPO . |

OTHER PUBLICATIONS

Koudelka et al, Voltammetry—A Powerful Tool for Evaluation Transducers, 1987 no month available.

Suzuki et al, Fabrication of an Oxygen Electrode Using Semiconductor Technology, Anal. Chem. (60) 1988, no month available, p. 1078.

Suzuki et al, Miniature Clark–Type Oxygen Electrode Sensors and Actuators, 1990, p. 297 no month available.

(List continued on next page.)

*Primary Examiner*—Bruce F. Bell

[57] ABSTRACT

A planar, solid-state electrochemical oxygen sensor having a substrate, conductive strips deposited on the substrate, and a dielectric layer insulating portions of the conductive strips except those portions which define a working electrode and at least one second electrode. The working electrode may be defined by an open printed region of the dielectric, or by a needle-punched or laser-burned hole or opening in the dielectric which exposes a small region of one of the conductive strips. A solid electrolyte contacting the electrodes is covered by a semipermeable membrane which may comprise an acrylonitrile butadiene copolymer or an acrylate-based copolymer. A sample chamber is defined by the membrane, a cover member, and a gasket therebetween, and has a volume of from about 1 to about 2 N.L. The gasket is formulated from the highly cross-linked polymerization product of epichlorohydrin. All sensor components are selected such that a sensor operable for at least 2 days under normal conditions is produced.

3 Claims, 17 Drawing Sheets

U.S. PATENT DOCUMENTS

| | | | |
|---|---|---|---|
| 4,571,292 | 2/1986 | Liu et al. | 204/415 |
| 4,613,422 | 9/1986 | Lauks | 204/419 |
| 4,661,411 | 4/1987 | Martin et al. | 428/421 |
| 4,734,184 | 3/1988 | Burleigh et al. | 204/409 |
| 4,739,380 | 4/1988 | Lauks | 357/25 |
| 4,871,439 | 10/1989 | Enzer et al. | 204/401 |
| 4,897,162 | 1/1990 | Lewandowski et al. | 204/1 |
| 4,908,112 | 3/1990 | Pace | 204/299 |
| 4,926,549 | 5/1990 | Yoshizawa et al. | 29/876 |
| 4,975,175 | 6/1990 | Karube et al. | 204/415 |
| 5,071,527 | 12/1991 | Kauffman | 204/434 |
| 5,120,421 | 6/1992 | Glaso et al. | 204/406 |
| 5,145,940 | 9/1992 | Wernet et al. | 528/226 |
| 5,185,922 | 2/1993 | Pendly et al. | 29/874 |
| 5,215,643 | 6/1993 | Kusanagi et al. | 204/426 |
| 5,444,188 | 8/1995 | Iwayama et al. | 29/846 |

OTHER PUBLICATIONS

Koudelka, Performance Characteristics of a Planar "Clark-Type" Oxygen Sensor, Sensors and Actuators 9 (1986). no month available.

Savnik et al, Miniature Multiple Cathode Oxygen Sensor for Medical and Biological Monitoring, AICHE Meeting Nov. 1981.

Pace et al, A Thick Film Multi-Layered Oxygen Sensor, E. I. DuPont de Nemours, 1985, p. 406 no month available.

Kuwata et al, A Solid State Oxygen Sensor Using Nafion Membrane, Chem. Lett., 1988, p. 1197 no month available.

Yan et al, Solid Polymer Electrolyte-Based Electrochemical Oxygen Sensor, Sensors and Activators, (19) 1989 p. 33 no month available.

Van der Linden et al, Array of Electrodes for Multi-Component Analysis, Anal. Proc., (26) 1989, p. 329 no month available.

Bechtold et al, Hybrid Integrated Chemical Multi-Element Sensors in Thick-Film Technology, Technisches Messen, (56) 1989 no month available.

Parthasarathy et al, Investigations of the O2 Reduction Reaction, J. Elec. Soc., (138) 1991, p. 916 no month available.

Yasuda et al, Electrochemical Characteristics of teh Planar Electrochemical Carbon Monoxide, Solid State Ionics, (40/41) 1990, p. 476 no month available.

Bethelheim et al, A New Polymer Ag/AgCl Reference Electrode, publication source unknown, date unknown no month or year available.

Chemical Sensing with State Devices, Madow & Morrison, Ion-Exchange Ceramics, see p. 455 and table 11.3, date unknown no month or year available.

Chemical Sensing with State Device, Madow & Morrison, Ion-Exchange Ceramics, see p. 455 and table 11.3, date unknown no month or year available.

Mallinckrodt Sensor Systemt—Technical Summary of GEM Technology, 1989 no month available.

Jain et al, Effect of Electrode Geometry on Sensor Response, Sensors and Actuators, (2) 1990, p. 111 no month available.

Zemel, Microfabricated Nonoptical Chemical Sensors, Rev. Sci. Instrum, (61) 1990, p. 1579 no month available.

Topics in Current Chem., pO2 Measurements, Springer Verley, v. 143, p. 55 no month or year available.

Shiavon et al, Amperometric Monitoring of Ozone in Gaseous Media, Anal. Chem., (62) 1990, p. 293 no month available.

Suzuki et al, Disposable Oxygen Electrodes Fabricated by Semiconductor Techniques, Sensors and Activators, 1990, p. 528 no month available.

Buttner et al, Microfabricated Amperometric Gas Sensors with an Integrated Design, Sensors and Materials, (2) 1990, p. 99 no month available.

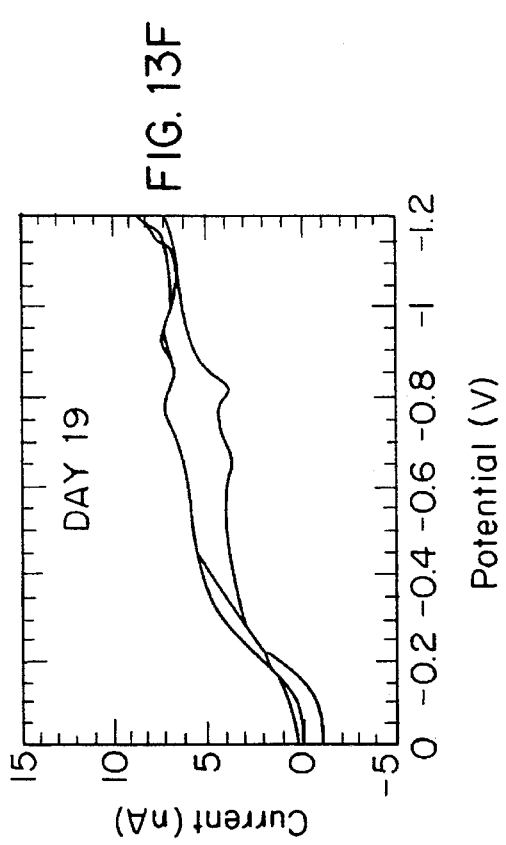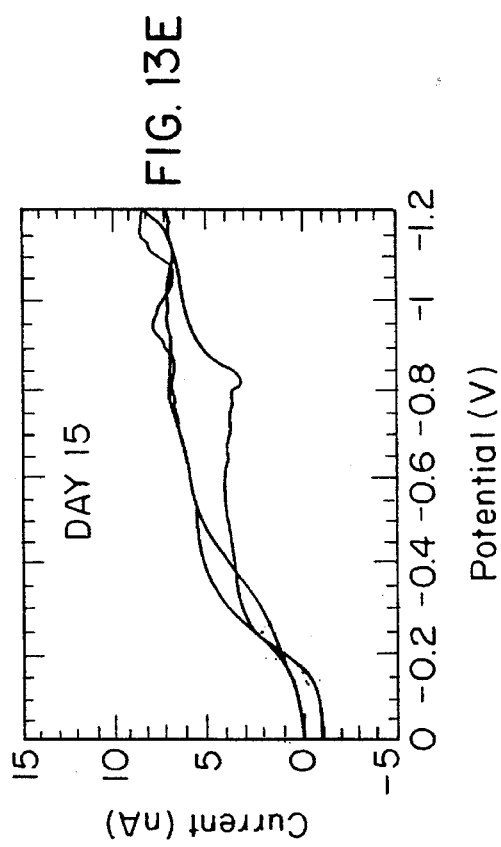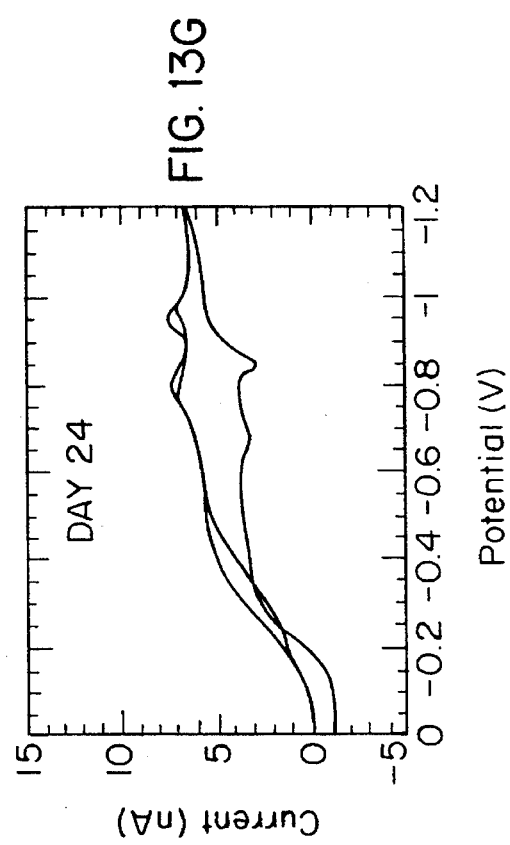

EXTENDED USE PLANAR SENSORS

This is a divisional of copending application(s) Ser. No. 08/209,081 filed on Mar. 9, 1994 which is a divisional application of U.S. Ser. No. 08/045,847 filed on Apr. 9, 1993, now U.S. Pat. No. 5,387,329.

FIELD OF THE INVENTION

The present invention relates generally to planar sensors, and more specifically to a planar electrochemical oxygen sensor that is small, is non-oxygen-depleting, is convenient and inexpensive to manufacture, and has a fast response time and has a long useful life.

TECHNICAL REVIEW

In the clinical setting, it is important to monitor certain blood analytes which are significant to normal physiological function and homeostasis. Such blood analytes include $pCO_2$, $pO_2$, tHb, pH, $Na^+$, $K^+$, $Cl^-$ and $Ca^{2+}$. The focus of the present invention is to sensors for the measurement of $pO_2$, i.e., the partial pressure of oxygen. The teaching of the present invention further extends to sensors for measuring other blood analytes and to sensors for use in other technical fields. Conventional approaches for doing so utilize a variety of electrochemical means such as two or three-electrode electrochemical sensors having liquid, solid, or gel electrolytes.

Conventional sensors are fabricated to be large, comprising many serviceable parts, or to be small, planar-type sensors which may be more convenient in many circumstances. The term "planar" as used herein refers to the well-known procedure of fabricating a substantially planar structure comprising layers of relatively thin materials, for example using the well known thick-film or thin-film techniques. See, for example, U.S. Pat. No. 4,571,292, and U.S. Pat. No. 4,536,274, both incorporated herein by reference.

The electrodes of such a sensor are conventionally addressed by an electrolyte covered by a gas permeable but liquid impermeable membrane such as teflon, polyethylene or polypropylene. As blood is placed in contact with the membrane, oxygen from the blood diffuses across the membrane, through the electrolyte solution, and is reduced at a cathode. The oxygen partial pressure of the sample is determined by measuring the resultant electrical current flowing through a circuit including the cathode and an anode. A three-electrode sensor may be employed, which maintains a constant voltage relationship between a working electrode (cathode) and a reference electrode by a feedback control, and is described in U.S. Pat. No. 4,571,292, referenced above. According to such a system, oxygen may be reduced at the working cathode, this reaction driven by the constant potential between the working and reference electrodes such that a reaction taking place at a counter electrode (anode) is simply the reverse of that occurring at the working cathode, that is, a non-electrode-consuming reaction.

With regard to both two and three-electrode sensors, it is desirable to manufacture a working electrode (cathode) to be very small. In this way, reduction of oxygen at the cathode is the rate-limiting step, and more accurate current output as a function of $pO_2$ is realized.

Additionally, the cathode is desirably manufactured to be very small so that the sensor exhibits non-depleting behavior, that is, fast, stir rate independent (time-independent) current response is realized. The principal of non-depletion is discussed in an article entitled "Voltammetric Microelectrodes", in *Current Separations*, 8, ½ (1987) by Jonathan O. Howell, and references therein. However, it is difficult to routinely and inexpensively manufacture a sensor having a working electrode small enough so as to be non-depleting.

In the clinical setting it is a goal, with respect to electrochemical blood analyte analysis, to maximize the data obtainable from a sample having a volume on the order of microliters. Fabrication of a very small sensor sample chamber for holding a sample in contact with a semipermeable membrane is desirable in this regard so that many tests may be performed, for example using a series of interconnected sensors each constructed to detect a different analyte, from one very small sample volume such as a capillary tube sample. However, as a sample chamber is made smaller, the concentration of contaminations in a sample from sensor components themselves, especially components defining a sample chamber, and/or certain reaction products of sensor function itself, is increased. Such contamination may result in premature sensor failure.

The lifetime of small planar sensors is commonly dictated by contamination of a semipermeable membrane by sample components or by impurities present in other sensor components which may leach into the membrane directly or via the sample. Such contamination commonly affects the permeability characteristics of the membrane, which may affect the linearity of sensor performance, or may allow the passage of species which may contaminate underlying electrolyte or electrodes.

An additional factor which may shorten sensor lifetime is delamination of various sensor components from other sensor components. These complications typically result in sensors that do not provide precise and reproducible current output at a given level of analyte concentration to which the sensor is exposed for an acceptable period of time. Thus, commercially-available planar electrochemical sensors for measuring analytes in blood such as oxygen generally fail after exposure to a limited number of samples.

Indicators which has been found by the inventors to determine sensor utility, and to monitor the useful life of a sensor, include sensor polarograms which differ drastically from those which the sensor exhibited when new and/or which contain spurious peaks attributable to impurities, and plots of current output versus analyte concentration which show unacceptable drift.

If it were possible to fabricate a semipermeable membrane for separating a sample area from an electrochemical sensing area that was relatively impermeable to species detrimental to the sensor, that was unaffected by any other sensor components, and was effective for a long period of time, sensor longevity would be increased.

Attempts have been made, for example, U.S. Pat. No. 4,734,184, issued Mar. 29, 1988, incorporated herein by reference, describes a disposable electrochemical sensor apparatus for measuring analytes in body fluid samples. A membrane is constructed to separate the sample area from the electrochemical sensor area and to pass analytes and species necessary for the sensing function, while preventing transport of undesirable species.

However, it remains a challenge in the art to formulate a membrane composition which exhibits a constant permeability to desired species over an extended period of time while maintaining impermeability to undesired species for the same length of time. Additionally, it is an added challenge to engineer into such a membrane desirable macroscopic physical properties such as durability and flexibility, while maintaining desirable microscopic physical properties that provide desirable permeability characteristics of the membrane.

Accordingly, it is a general purpose of the present invention to provide a means and method of measuring the concentration of an electrochemically active species such as oxygen in a fluid such as blood, using a small electrochemical sensor which is relatively simple and inexpensive to manufacture, is non-depleting with respect to the active species measured, and has a relatively long useful life.

SUMMARY OF THE INVENTION

The foregoing and other objects and advantages of the present invention are achieved by providing a semipermeable membrane for use in a planar oxygen sensor or the like, comprising a polymer which may be deposited from organic solution and which itself comprises the polymerization product of at least one nitrile monomer unit and at least one conjugated diene monomer unit. In an alternate embodiment, the membrane comprises the polymerization product of at least one acrylate monomer unit. The membrane is desirably impermeable to liquid water, but rapidly permeable to water vapor. Additionally, it is preferred that the membrane for an oxygen sensor be impermeable to ions and other blood constituents, and have limited permeability to oxygen. The membrane functions usefully for a period of at least 2 days, preferably 10 days, and more preferably 15 days under normal sensor operation when used with the inventive oxygen sensor. Sensors fabricated in accordance with a particularly preferred embodiment, containing a particularly preferred membrane, have been demonstrated to function usefully for at least 60 days under normal operation. Normal sensor operation is defined hereinbelow.

It is another object of the present invention to provide a gasket for forming a liquid and gas impermeable seal between a semipermeable membrane and a cover member which together define in part a sample chamber of an electrochemical sensor. The gasket comprises a highly cross-linked polymerization product of an epoxy compound and a hydrophilic monomer according to one embodiment. Preferably, the gasket has a Shore A hardness of from about 10 to about 100, an oxygen permeability of less than 20 Barrers, and is liquid impermeable and formulated to be substantially free of mobile extractable materials which could leach into the membrane affecting physical or permeability characteristics therein. The gasket is further formulated to be substantially free of mobile sulfides and battery metals, and is effective in forming and maintaining said seal for at least 2 days, preferably 10 days, and more preferably 15 days under normal sensor operation.

It is another object of the present invention to provide a sample chamber for containing a physiological fluid, the $PO_2$ of which is to be measured, which chamber is defined by a semipermeable membrane overlaying an electrochemical sensor, a cover member having at least one passageway through which the sample fluid may pass, and at least one gasket between the cover member and the membrane which seals the chamber. The gasket is selected so as to be free of any extractable materials, or such that any extractable materials present do not leach into the membrane in a way that affects the desirable features of the membrane. The gasket is further selected so as to be substantially free of species which, if they were to leach into a sample, would interfere with the electrochemical measurement of a particular analyte therein, or which would adversely affect the electrolyte, electrodes, or other components of the electrochemical sensor. According to this embodiment, the gasket and membrane are further selected so as to have sufficient flexibility characteristics to form a sealed junction at their interface, which junction remains sealed for the lifetime of the sensor, and which seal does not adversely physically affect the gasket or the membrane.

It is another object of the invention to provide a novel means and method for forming a small, electrically addressable area of electrically conductive material for use as a microelectrode or the like. According to the method, an electrically conductive material is placed on a substrate, and at least a portion of the material covered with an electrically-insulating non-porous material, i.e., a dielectric material. A small discontinuity is formed in the electrically insulating material using a needle punch to expose a small, electrically-addressable area of the electrically conductive material, and defining a microelectrode. According to a specific method, a needle punch is in electric communication with the electrically conductive material. When the needle punch penetrates the electrically insulating material and contacts the electrically conductive material, an electrical circuit is formed, indicating such penetration, and the needle punch is withdrawn from the electrically conductive material. The apparatus may be designed so that the needle is withdrawn at any of a variety of positions relative to the surface of the electrically conductive material.

It is another object of the present invention to provide a means and method for forming a two or three-electrode solid-state planar oxygen sensor using thick or thin-film techniques, which sensor is non-depleting, is relatively inexpensive, has a fast response time, is constructed to measure blood samples having volumes on the order of microliters, and has a lifetime on the order of days or months.

It is another object of the present invention to provide a solid-state planar oxygen sensor comprising an electrically nonconductive substrate, a first electrically conductive material adhered to a first portion of said substrate, at least a portion of said first conductive material being covered with an electrically insulating dielectric coating and at least one portion of said first conductive material remaining uncovered by said electrically insulating dielectric coating, said uncovered portion of said first conductive material defining a working electrode area, a second electrically conductive material adhered to a second portion of the substrate, a portion of said second conductive material being covered with the electrically insulating dielectric coating and at least one portion of said second conductive material remaining uncovered by said electrically insulating dielectric coating, said uncovered portion of said second conductive material defining a counter electrode area, a third electrically conductive material adhered to a third portion of the substrate, a portion of said third conductive material being covered with the electrically insulating dielectric coating and at least one portion of said third conductive material remaining uncovered by said electrically insulating dielectric coating, said uncovered portion of said third conductive material defining a reference electrode area, a hygroscopic solid electrolyte provided on at least the working electrode area and the counter electrode area, said electrolyte having a swell value of less than two times its dry volume when provided with water, a semipermeable membrane covering said electrolyte having an oxygen permeability of less than 8 Barrers, a cover member covering said semipermeable membrane and having a recess formed therein, said recess having a perimeter facing the membrane and at least one passageway connected to the recess, and a gasket contacting the recess perimeter and the membrane to form a seal therebetween, the gasket, cover member, and membrane defining a sample chamber.

It is another object of the present invention to provide a solid-state planar oxygen sensor comprising an electrically nonconductive substrate, a first electrically conductive material adhered to a first portion of said substrate, at least a portion of said first conductive material being covered with an electrically insulating dielectric coating and at least one portion of said first conductive material remaining uncovered by said electrically insulating dielectric coating, said uncovered portion of said first conductive material defining a working electrode area, a second electrically conductive material adhered to at least a second portion of the substrate, a portion of said second conductive material being covered with the electrically insulating dielectric coating and at least one portion of said second conductive material remaining uncovered by said electrically insulating dielectric coating, said uncovered portion of said second conductive material defining a counter electrode area, an electrolyte provided on at least the working electrode area and the counter electrode area, and polymeric semipermeable membrane covering the electrolyte, said membrane comprising the polymerization product of at least one monomer having the formula $CH_2=C(R_1)(COOR_2)$, where $R_1$ and $R_2$ are each selected from the group consisting of hydrogen, hydrocarbon groups, and alcohol groups and $R_1$ and $R_2$ can be the same or different, or the polymerization product of at least one nitrile-containing monomer and at least one conjugated diene monomer.

It is another object of the present invention to provide an electrochemical sensor comprising electrochemical means for detecting an analyte in a test sample, a semipermeable membrane covering said electrochemical means, said membrane being permeable to said analyte and to species necessary for the functioning of said electrochemical means, a cover member covering said semipermeable membrane and having a recess formed therein, said recess having a perimeter facing the membrane and at least one passageway connected to the recess, and a gasket contacting the recess perimeter and the membrane to form a seal therebetween, the gasket, cover member, and membrane defining a sample chamber.

It is another object of the present invention to provide a method for forming a microelectrode for use as a working electrode in a planar, solid-state oxygen sensor or the like, comprising the steps of selecting an electrically nonconductive substrate, combining said substrate with an electrically conductive material with said electrically conductive material forming a layer adjacent said electrically nonconductive substrate, coating at least a portion of the electrically conductive material with an electrically insulating material, puncturing the electrically insulating material to form at least one hole or opening or opening therein with a needle in communication with electric circuit means in communication with the electrically conductive material, moveable between a first position and a second position in which the electric circuit means generates a signal withdrawing the needle when the signal is generated, said insulating material being selected so as to firmly adhere to the conductive material such that when the hole(s) or opening(s) is formed an exposed, electrically addressable portion of the electrically conductive material is created, defining at least one electrode having a size defined by the cross-sectional area of the hole or opening.

It is another object of the present invention to provide a method for forming a microelectrode for use as a working electrode in a planar, solid-state oxygen sensor or the like, comprising the steps of selecting an electrically nonconductive substrate, combining said substrate with an electrically conductive material with said electrically conductive material forming a layer adjacent said electrically nonconductive substrate, coating a surface of the electrically conductive material with an electrically insulating material selected so as to firmly adhere to the conductive material, passing a needle in communication with electric circuit means in communication with the electrically conductive material through the electrically insulating material, which needle is movable between a plurality of positions relative to the surface, some of which positions cause the electric circuit means to generate signals, and withdrawing the needle when a predetermined signal is generated indicating a predetermined relative position.

It is another object of the present invention to provide an electrochemical oxygen sensor having an improved semipermeable membrane comprising the polymerization product of at least one nitrile-containing monomer and at least one conjugated diene monomer.

It is another object of the present invention to provide an electrochemical sensor having an improved semipermeable membrane comprising the polymerization product of at least one monomer having the formula $CH_2=C(R_1)(COOR_2)$, where $R_1$ and $R_2$ are each selected from the group consisting of hydrogen, hydrocarbon groups, and alcohol groups and $R_1$ and $R_2$ can be the same or different.

It is another object of the present invention to provide a method for selecting an electrically-conductive material for use in an electrochemical sensor or the like, comprising measuring the polarogram of said material to determine the shape of said polarogram in a predetermined potential region within which said sensor is designed to operate, and evaluating said polarogram in said predetermined region to determine whether said polarogram is substantially free of excessive peaks.

It is another object of the present invention to provide an electrochemical sensor having a semipermeable membrane, electrochemical means on a first side of said membrane for detecting an analyte in a sample, and a sample chamber on a second side of said membrane for receiving said sample, said chamber defined in part by said second side of said membrane and a cover member having a recess formed therein, said recess having a perimeter facing said second side of said membrane, and being improved by having a gasket for forming a liquid and gas impermeable seal between said second side of said semipermeable membrane and said cover member recess perimeter, said gasket comprising a durable organic polymer or copolymer which does not creep or flow when stressed, which has a low durometer rating, which is gas impermeable, and which is slightly hygroscopic and thus swells slightly in the presence of solution containing water.

It is another object of the present invention to provide a composition comprising the polymerization product of at least one monomer having the formula $CH_2=C(R_1)(COOR_2)$, where $R_1$ and $R_2$ are each selected from the group consisting of hydrogen, hydrocarbon groups, and alcohol groups and $R_1$ and $R_2$ can be the same or different, at least one monomer selected from the group consisting of those having the formulas $CH_2=C(R_1)(CONR_2R_3)$, $CH_2=C(R)_1(OCOR_2)$, where $R_1$, $R_2$, and $R_3$ are each selected from the group consisting of hydrogen, hydrocarbon groups, and alcohol groups and $R_1$, $R_2$, and $R_3$ can be the same or different, and at least one nitrile-containing monomer.

It is another object of the present invention to provide a composition comprising the polymerization product of at least one monomer having the formula $CH_2=C(R_1)(COOR_2)$, where $R_1$ is selected from the group consisting of hydrogen and lower alkyl groups, $R_2$ is selected from the group consisting of linear, branched and cyclic hydrocarbons and alcohols of from 1 to 20 carbon atoms, $R_1$ and $R_2$ being the same or different, said monomer being present in an amount of from about 20% to about 80% by weight based on the weight of the composition at least one nitrile-containing monomer, said nitrile-containing monomer being present in an amount of from about 15% to about 80% by weight, and at least one monomer selected from the group consisting of those having the formula $CH_2=C(R_1)(OCOR_2)$ where $R_1$ and $R_2$ are each selected from the group consisting of hydrogen, lower alkyl groups and lower alcohols and $R_1$ and $R_2$ can be the same or different, those having the formula $CH_2=C(R_1)(CONR_2R_3)$ where $R_1$, $R_2$, and $R_3$ are each selected from the group consisting of hydrogen and lower alkyl groups and $R_1$, $R_2$, and $R_3$ can be the same or different, and a combination of the two.

It is another object of the invention to provide a method for evaluating the adherence between an electrically conductive material and an electrically insulating dielectric layer contacting the electrically conductive material, the dielectric material arranged so as to expose a specific region of said electrically conductive material defining an electrode, comprising biasing the electrode at a potential with a second electrode, said electrode and second electrode being contacted by an electrolyte; holding the potential constant over a predetermined period of time; measuring the resultant current output at said potential over said period of time; and determining whether said current output is substantially steady and substantially free of variation.

It is another object of the invention to provide a method of adjusting the oxygen permeability of a semipermeable membrane comprising a copolymer of a nitrile-containing monomer and a conjugated diene, comprising: adding a predetermined quantity of a species selected from the group consisting of a vinyl halide, a vinylidene halide, a copolymer comprising vinyl halide and a nitrile-containing monomer, a copolymer comprising vinylidene halide and a nitrile containing monomer, or a combination of any of the above, to said nitrile/conjugated diene copolymer, to form a mixture of copolymers, said predetermined amount being selected so as to adjust the oxygen permeability to a predetermined level.

It is another object of the invention to provide a method for evaluating the durability of an electrochemical sensor comprising: measuring the polarogram of said sensor to determine the shape of said polarogram in a predetermined potential region within which said sensor is designed to operate, and evaluating said polarogram in said predetermined region to determine whether said polarogram is substantially free of excessive peaks.

These and other objects in view, as will be apparent to those skilled in the art, the invention resides in the combination of elements set forth in the specification and covered by the claims appended hereto.

BRIEF DESCRIPTION OF THE DRAWINGS

The above and other features, objects and advantages of the present invention will be better understood from the following specification when read in conjunction with the accompanying drawings, in which:

FIGS. 13A–13G illustrate cyclic voltamograms, taken after various periods of use, of a sensor fabricated according to one embodiment of the present invention;

DESCRIPTION OF PREFERRED EMBODIMENTS

Figure 1:
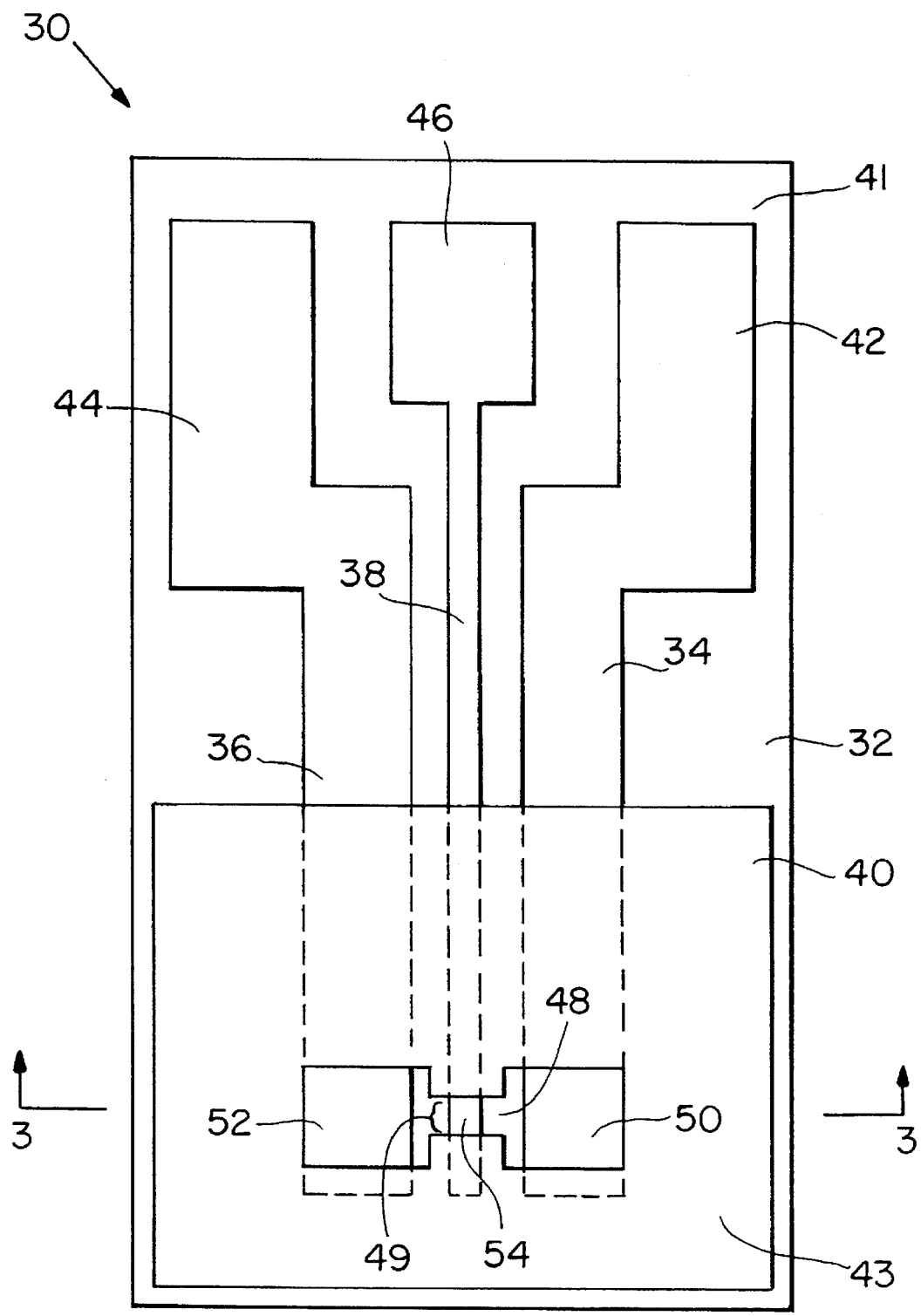
FIG. 1 is a top view of a partial assembly of a preferred embodiment of a planar oxygen sensor according to the present invention with electrolyte, membrane, gasket and cover member removed.

A planar oxygen sensor 30 in accordance with a preferred embodiment of the present invention is illustrated in FIG. 1 and includes substantially planar substrate 32, conductive metal strips 34, 36, and 38 deposited thereupon, and dielectric layer 40 deposited on substrate 32 so as to cover portions of conductive strips 34, 36, and 38, while leaving portions of some of the conductive strips uncovered.

Substrate 32 is formed from any substantially electrically insulating material such as ceramic, glass, refractory, polymers or combinations thereof. Formation of such an insulating substrate as a mechanical support or base is common knowledge to those of ordinary skill in the art. In the preferred embodiment, the substrate comprises approximately 96% alumina and approximately 4% glass binder. A suitable material comprising the preferred composition is available from Coors Ceramic Company, Grand Junction, Colo. Although in the preferred embodiments of the present invention a single substrate forms the foundation of the oxygen sensor, a plurality of substrates each supporting separate sensor components, and/or helping to support sensor components supported by other substrates, could be employed.

Conductive strips 34, 36, and 38 are deposited atop substrate 32 so as to extend from a first end 41 thereof to a second end 43 thereof in a preferred embodiment. At first end 41, the conductive strips are typically deposited so as to be wide enough to define contact pads 42, 44, and 46, respectively. At second end 43, the conductive strips are typically deposited so as to be somewhat narrower, exposed regions of which may define electrodes, as described below.

Conductive strips 34, 36, and 38 may be deposited using the well known thin or thick-film techniques. Typically, a compound including a metal is applied via typical thick-film screening to substrate 32, and the applied compound and substrate are then fired to sinter the active metal and to co-adhere the active metal to the substrate. The electroactive metal may comprise any conductive metal, for example, silver, platinum or gold, which is not oxidized or reduced in a potential range in which oxidation or reduction of any species to be measured occurs. In the case of an oxygen sensor, electroactive metals should not be susceptible to oxidation in the range of from 0 to −1200 millivolts (mV) vs. silver/silver chloride. Additionally, materials selected for fabrication of conductive strips 34, 36, and 38 are desirably selected so as to be free of any impurities such as battery metals (that is, ones that are electrochemically active in water) which are typically present in off-the-shelf materials commercially available for wire bonding, etc.

Many thick-film pastes are commercially available, such as a silver pastes available as part number 3571UF/Ag from Metech Company, of Elverson, Pa. (Metech), and part number 6061/Ag from E. I. DuPont De Nemours & Company (DuPont) of Wilmington, Del.; silver chloride available as part numbers 2539/Ag/AgCl or PC10299 from Metech; gold pastes available as part number PC10231/Au from Metech, part number 5715H/Au from DuPont, and part number JM1301/Au from Johnson Matthey of West Deptford, N.J.; and platinum paste available as part number PC10208/Pt from Metech.

In the selection of specific pastes for use as electrodes in the invention, and in one embodiment electrodes may be continuous with conductive strips, and with specific regard to conductive strip 38 which defines in part a working electrode, as described below according to one embodiment, it is advantageous to conduct a preliminary evaluation in which a polarogram exhibited by the working electrode material is recorded in order to assess manufacturing, quality control, and product specifications. As is well known, a polarogram may be recorded by biasing an electrode against a reference in the presence of an electrolyte, varying the voltage within a predetermined range, and recording the current output as a function of voltage.

As discussed above, it has been determined by the inventors that a determination of sensor utility may be made based on indicators including polarograms exhibited by the sensor. Additionally, it has been determined in accordance with the present invention that a determination of a suitable candidate for use as a material for fabrication of the electrodes, especially a working electrode (described below) and in one embodiment conductive strip 38, may also be made based upon a polarogram exhibited by the material. A suitable candidate as a material for fabrication of an electrode, especially a working electrode (and conductive strip 38 according to one embodiment) advantageously will exhibit a polarogram having a plateau in a region in which the sensor will typically be polarized during electrochemical analysis. According to a preferred embodiment of the present invention, this means that a suitable material will exhibit a relatively flat current vs. voltage plot in the region of approximately −0.800 V+/−0.300 volts (V) vs. silver/silver chloride. It is to be understood that the choice of electrical potential in electrochemical analyses of sensor components, for example polarogram-based analyses, is not critical to the present invention. Any potential setting may be chosen in accordance with the desirable operational parameters described herein.

If, during sensor operation, the voltage at which the working electrode was set could be held absolutely constant, there would be no need for an electrode material polarogram plateau. However, as absolute voltage control is not practical, a plateau is desirable. As used herein, the terms "plateau" and "relatively flat current vs. voltage plot" are meant to define a region of the curve defined by the polarogram in which inherent instrumental and experimental voltage fluctuation does not result in current readout which fluctuates outside of an acceptable margin of error, in the operation of some sensors a plateau may not be observed but function properly as long as voltage fluctuation does not vary outside an acceptable margin of error.

It has also been determined in accordance with the invention that evaluation of material for electrode use based on the above-noted polarogram analysis is advantageous as a polarogram may exhibit peaks indicative of impurities present in the material. It is to be understood that a peak in such a polarogram is not necessarily indicative of an unsuitable material. For example, a peak may merely indicate electrochemistry associated with the consumption of an impurity, and indicating a material well-suited for electrode use. However, a peak may be indicative of the presence of an impurity generated from, or within, the material during the electrochemical measurement, and thus may indicate that a material is unsuitable.

With specific regard to conductive strip 38, which defines in part a working electrode, a preferred material is a very high purity platinum thick-film paste. Conductive strip 34 preferably comprises a thin layer of silver deposited atop substrate 32 with a layer of silver chloride deposited thereupon in the electrode region, discussed below, to create a reference electrode. Alternately, a silver layer deposited as conductive strip 34 may be electrochemically oxidized in the presence of sufficient chloride ion to form a silver chloride layer atop a silver layer for use as a reference electrode. Such deposition or electrochemical formation of a silver/silver chloride reference electrode is well known in the art. Conductive strip 36 comprises a gold thick-film paste or a platinum thick-film paste in preferred embodiments.

Employment of a silver reference electrode is within the scope of the present invention. Modification of the teachings of the present invention with respect to voltage settings, upon the substitution of a silver reference electrode for a silver/silver chloride reference electrode, would be easily made by one of ordinary skill in the art.

At the second end 43 of substrate 32, dielectric layer 40 is deposited so as to cover portions of conductive strips 34, 36, and 38, while containing an open printed region 48 which leaves portions of the conductive strips uncovered so as to define reference electrode 50, (if present), counter electrode 52, and working electrode 54. Material selected for fabrication of the dielectric layer 40 is desirably electrically insulating and non-porous, free of impurities which may be subject to oxidation or reduction in the potential range of any species or analyte to be measured, as described above, and is further selected so as to be free of mobile ions that would potentially carry charge and interfere with the activity of any electrolyte employed in the sensor. Further, dielectric 40 is selected so as to firmly adhere to substrate 32 and conductive strips 34, 36, and 38, so as to allow electrodes 50, 52, and 54 to be electrically addressable, while effectively electrically insulating portions covered by the dielectric. Materials such as ceramics, glass, refractory materials, polymeric materials, or combinations thereof are well known as dielectric materials and are suitable for use as a dielectric in the present invention.

With respect to materials advantageously selected for fabrication of conductive strips 34, 36, and 38, it is noted that material selection becomes less important in regions of the strips which define contact pads 42, 44, and 46 and which connect the bonding pads to regions which define electrodes. For example, the contact pads and regions of the conductive strips connecting them to the electrodes may be fabricated from any conducting material that adheres to substrate 32 and that does not interfere with the electrical insulation function of dielectric layer 40. According to one embodiment, the contact pads and regions of the conductive strips connecting them to the electrodes are fabricated from a gold paste.

In addition to the material selection parameters discussed above, and as discussed with respect to selection of the dielectric material, it is advantageous in the fabrication of an extended-use sensor to select materials for fabrication of the substrate, the conductive strips, and the dielectric layer such that good adherence is achieved between adjacent layers, that is, delamination is minimized. If good adherence is not achieved reference, counter, and working electrodes 50, 52, and 54 will not be well-defined by open printed region 48, in one embodiment as defined by a screen used in the thick-film deposition process, and disadvantageous electrochemistry will result.

Preliminary electrochemical analysis may also be used to evaluate adherence between various materials according to the following method. An electrolyte is applied to the reference, counter, and working electrodes 50, 52, and 54 of the sensor as described above. The sensor is biased at a potential between the working electrode and the counter electrode, and a resultant current output level at constant voltage is observed over time. If the current output level is substantially steady and substantially free of variation, good adherence between adjacent layers is indicated. If delamination occurs, specifically, delamination between dielectric layer 40 and conductive strips 34, 36, and/or 38 where open printed region 48 defines electrodes 50, 52, and 54, this may be indicated by spurious peaks and other discontinuities in the current output level. Typically, such peaks and/or discontinuities take the form of a sharp, spontaneous rise from a baseline steady-state current, followed by gradual current tapering to a slightly higher steady-state current than the baseline current. Thus, testing of sensors and electrodes in such a manner gives rapid indication as to whether or not a particular combination of insulating material and conductive material shows sufficient adherence to define an electrode, particularly a small, working electrode in accordance with the methods of the present invention. Generally, selection of materials for deposition as adjacent layers which have similar coefficients of linear expansion may prevent delamination to some extent.

Figure 2:
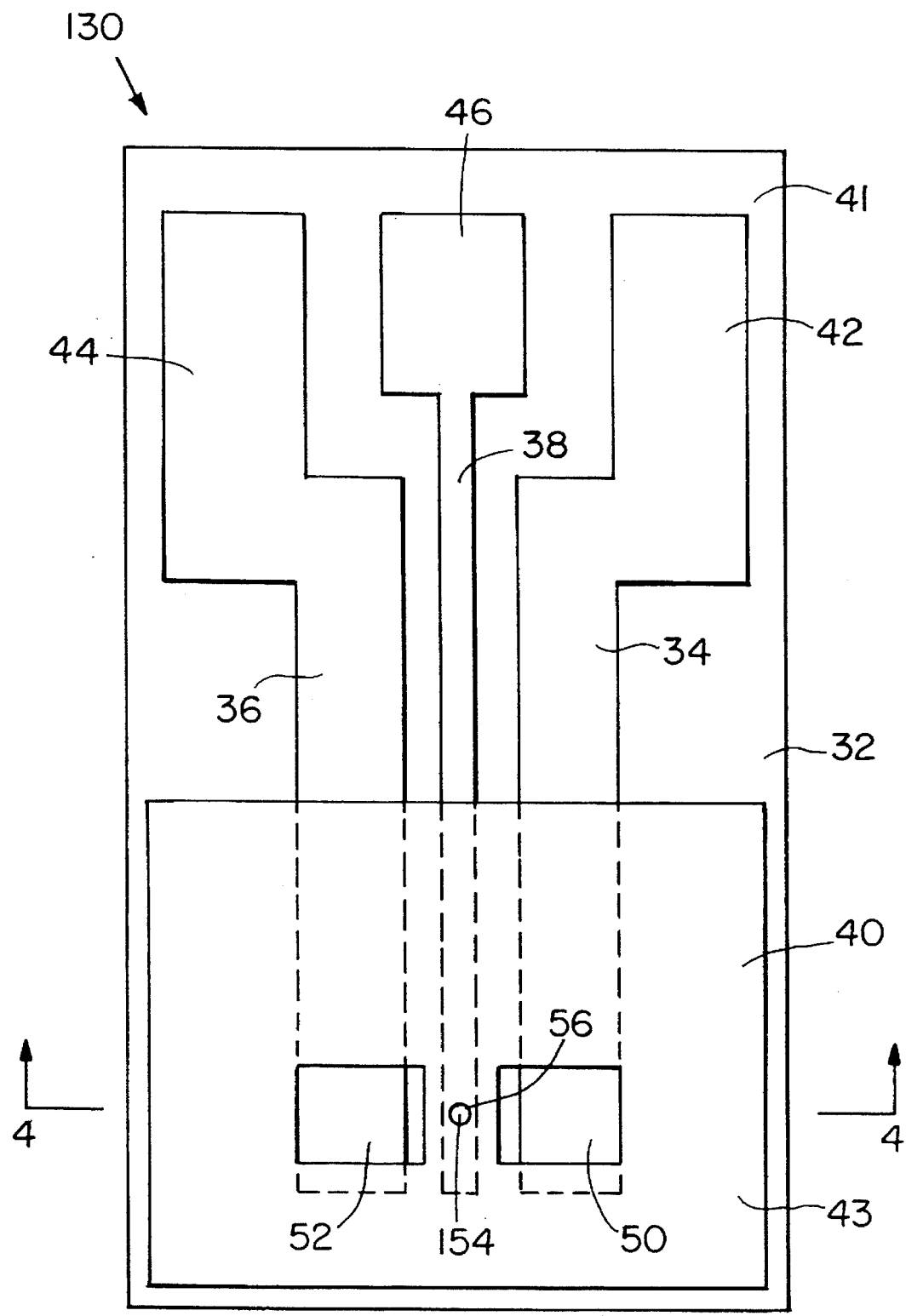
FIG. 2 is a top view of a partial assembly of an alternate embodiment of a planar oxygen sensor according to the present invention with electrolyte, membrane, gasket and cover member removed.

An alternate embodiment of the present invention is illustrated at 130 in FIG. 2. In FIG. 2 and in all the accompanying figures, elements of the present invention common to several figures are represented by common numerical designations. Referring to FIG. 2, dielectric layer 40 is deposited so as to expose portions of conductive strips 34 and 36, defining reference electrode 50 and counter electrode 52, respectively, but conductive strip 38 is entirely covered by dielectric 40 at the second end 43 of substrate 32. At least one small hole(s) or opening(s) 56 is then formed in the dielectric layer 40 so as to expose an area of conductive strip 38 which defines a working electrode 154.

Hole(s) or opening(s) 56 may be formed according to a variety of methods. According to one method, a laser is fired at dielectric layer 40 to form hole or opening 56. The laser and dielectric may be selected such that the wavelength of radiation emitted by the laser is absorbed by dielectric 40 to a degree sufficient to efficiently form the hole or opening 56 therein. A dielectric selected so as to absorb laser radiation to the greatest extent possible will result in a hole or opening 56 having a shape that corresponds closely with the shape of the cross-sectional area of the laser beam, as the hole or opening may be burned rapidly and efficiently. Formulating a dielectric such that the wavelength of radiation emitted by the laser is absorbed to a high degree may be effected by, for example, introducing pigments into the dielectric formulation. Such introduction of pigment should be made in accordance with the teachings herein regarding mobile species which may have an electrochemical effect or a physical effect on sensor components. A clear dielectric may also be selected, in which case hole or opening 56 would be formed as laser radiation would be absorbed by conductive strip 38, and overlaying dielectric layer 40 would be heated thereby. Thus, according to the method, a cross-sectional laser beam area being known, a working electrode having a predetermined size and shape may be defined.

Although hole or opening 56 is generally substantially circular when formed according to this embodiment, it need not be. For example, a laser may be oriented such that the laser beam strikes dielectric layer 40 at an angle other than a perpendicular angle. In such a case, hole or opening 56 may be elongated or oval-shaped. Additionally, the laser need not be stationary during firing, but may be moved during firing as to form an elongated or line-shaped hole. A plurality of holes or openings may be formed as well to create a plurality of small working electrodes. Such manipulation in concert with a particular selection of wavelength and laser focal adjustment may advantageously be utilized to create any desired size and shape of hole or opening 56 defining working electrode 154.

According to another method of formation of hole(s) or opening(s) 56, and referring still to FIG. 2, a needle is used to puncture dielectric 40 above conductive strip 38. As used herein, the term "needle" is understood to mean any instrument such as a needle, drill bit, ultrasonic tool, or the like. According to a preferred embodiment, a tungsten carbide needle having a tip radius of about 12 microns is employed. As noted herein, it is desirable to form a very small hole or opening 56 such that a very small working electrode 154 may be defined. However, using a needle to puncture material to expose an underlying layer may result in deformation of the surface exposed. Specifically, unless the needle is immediately withdrawn as soon as it contacts the surface of the material to be exposed, a depression in the material may be formed by the tip of the needle, resulting in essentially greater surface area exposed. Such precise needle control, especially if the needle is to puncture a series of holes or openings in imprecisely positioned articles, may be a complication.

Therefore, according to one method, a needle is provided in communication with electric circuitry, which electric circuitry is also in contact with conductive strip 38 via contact pad 46. Dielectric 40 is punctured by the needle until the needle contacts conductive strip 38, closing an electrical circuit including the needle, conductive strip 38, and the electric circuitry. When the circuit is closed, a signal is sent to controlling apparatus which immediately withdraws the needle from dielectric 40. In this way, the size of hole or opening 56, and the resultant size of electrode 154, is minimized and controlled. The electrical circuitry employed may be any conventional analog or digital circuitry, and is advantageously controlled by computer.

According to a preferred method, sensor 130 is mounted on an X-Y-Z table such as are available from Asymtek Corporation of Carlsbad, Calif., and is positioned such that a needle may puncture dielectric 40 directly above conductive strip 38. According to one embodiment, a needle assembly is mounted on a weighted ball slide which may be adjusted with respect to the downward force applied onto the needle by removing or adding weight. The needle and conductive strip 38 are connected by electric circuitry in communication with a computer, and when the needle contacts conductive strip 38, the computer commands the ball slide motor to immediately reverse direction and the needle is immediately withdrawn. It is to be understood that other methods of controlled downward force on the needle are within the scope of the present invention. For example, the needle may be mounted on a piezoelectrically-controlled device, such devices typically being capable of controlled motion to within one mm. Other modifications of downward force control known to those of ordinary skill in the art could be employed as well.

The method is applicable to the formation of microelectrodes of a variety of types, designed for a variety of uses, including other uses in the microelectronic arts, for example, any electrically conductive material may be coated with an electrically insulating material, and a hole or opening punctured in the electrically insulating material to form the electrode. The needle may be movable between a first position in which the needle is not in contact with the electrically insulating material, and a second position in which the needle has punctured the electrically insulating material and is contact with the electrically conductive material, at which point an electric circuit is closed, generating a signal which actuates apparatus causing the needle to be withdrawn.

Alternatively, the needle may be movable between a plurality of positions relative to the surface of the electrically conductive material, some of which positions cause an electric circuit in contact with the needle and the conductive material to generate signals. For example, signals may be generated only at particular threshold resistivity levels, and in this manner, the depth of penetration of the needle into the conductive material may be regulated by allowing a signal generated at the desired depth of penetration to actuate apparatus causing the needle to be withdrawn. In this manner, selecting a conductive material which may be penetrated to some extent by the particular needle selected may result in needle penetration, and a resultant depression may be formed in the surface of the conductive material to one of a variety of predeterminable depths, defining a variety of predeterminable electrode areas. In this manner, microelectrodes having precisely controlled surface areas may be produced. Control of the depth of needle penetration into the electrically conductive material may be based upon resistivity of a circuit including the needle and the electrically conductive material, as mentioned above, or may be based upon adjusting the ratio of the weight applied to a weighted ball slide to the time which an electric controlling circuit allows the weighted ball slide to apply force to the needle.

According to the needle-punch method, a dielectric is advantageously selected so as to be amenable to puncture. That is, a polymer dielectric having a predetermined softening point may be selected, and it may be advantageous to heat the needle or the stage upon which a sensor is mounted, or both, so as to soften the polymer dielectric during puncture. When the needle, stage, or both are heated so as to soften the polymer dielectric during puncture, care should be taken such that excessive heat is not applied, which heat would cause adjacent sensor layers to delaminate. Particularly, any heating should be carried out so as not to cause delamination between the dielectric and the electrically conductive material.

Materials suitable for use as dielectric 40 according to the needle-punch method of the present invention may comprise any of a variety of compounds, for example polymer compounds which adhere well to conductive strips 34, 36, and 38, especially during and after the needle punching step. Suitable polymers may be selected from those in the alkyd resin family (unsaturated polyester resin) and may contain phthalic anhydride, maleic anhydride, various glycols, and may additionally contain unsaturated oils. Other suitable polymer precursors for dielectric formation are siloxane copolymers or siloxane-imide copolymers. A preferred material is available as part number ESL 240 SB from Electro Science Laboratories in King of Prussia, Pa.

According to the needle punch method described herein, as in the case of the laser hole or opening formation method, a plurality of holes 56 may be formed in dielectric 40 defining a plurality of working electrodes 154, and a variety of shapes and sizes of hole or opening 56 may be created. For example, a needle may be oriented at an angle relative to dielectric layer 40 other than a perpendicular angle during punching, or may be moved relative to the dielectric layer during hole or opening formation. Thus, oval-shaped, elongated, or line-shaped working electrode or electrodes 154 may be formed.

Due to the physical disruption of dielectric layer 40 and, in some instances, the underlying electrically conductive strip 38 inherent in the laser hole and needle punch hole formation methods, the above-described electrochemical delamination analysis may be advantageously carried out after formation of holes or openings according to those methods.

Figure 3:
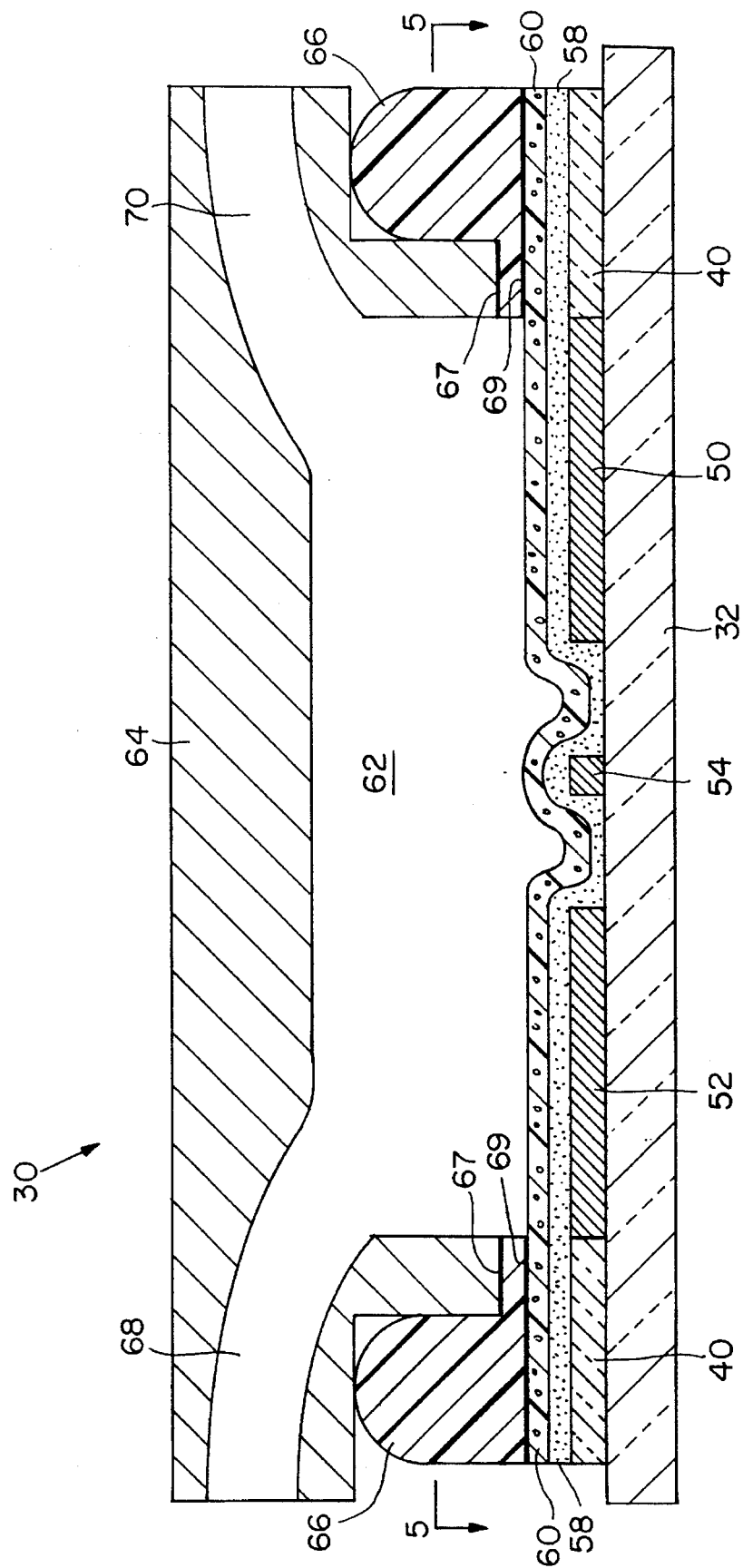
FIG. 3 is a cross-sectional view through line 3—3 of FIG. 1, with electrolyte, membrane, gasket and cover member in place.
Figure 4:
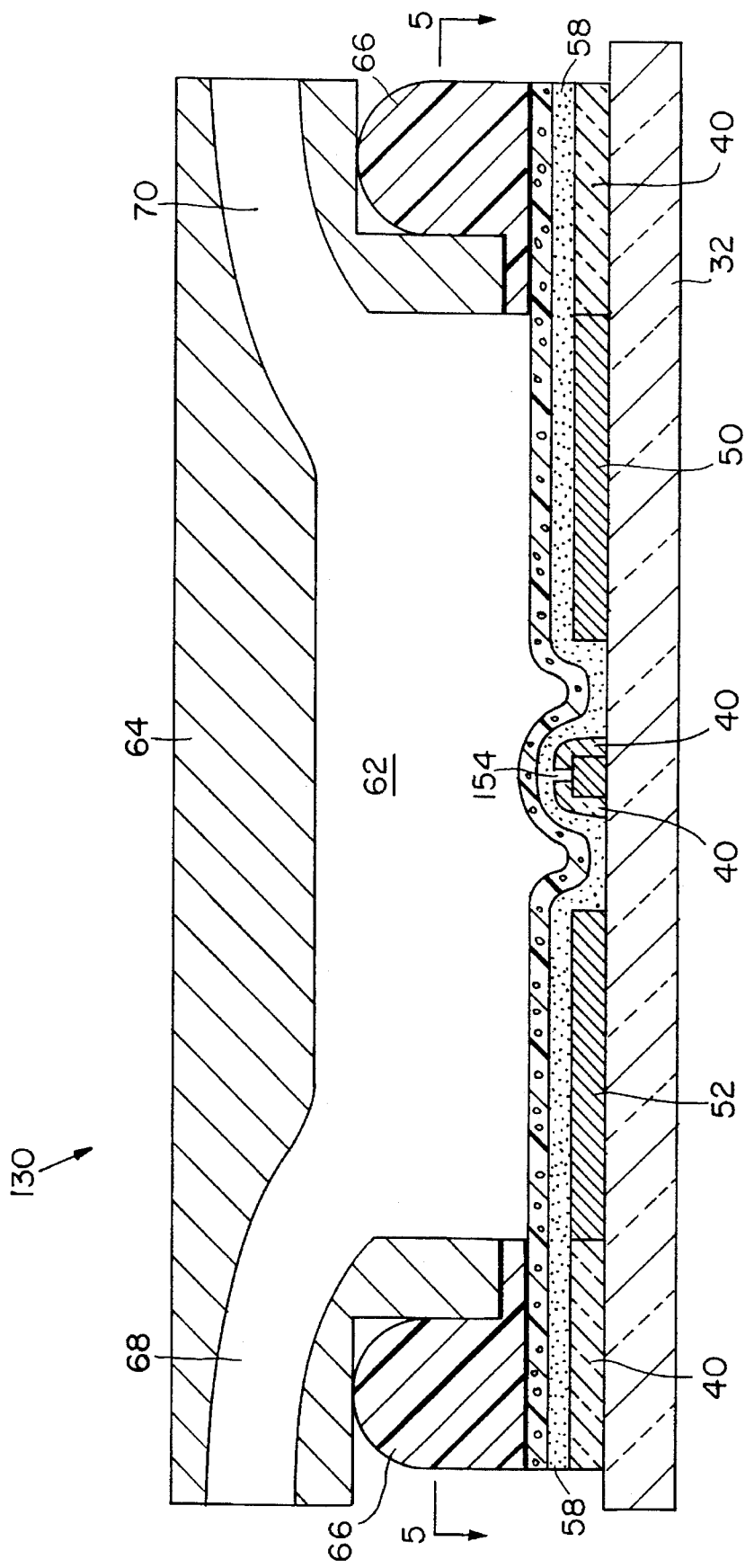
FIG. 4 is a cross-sectional view through line 4—4 of FIG. 2, with electrolyte, membrane, gasket and cover member in place.

Referring now to FIGS. 3 and 4, embodiments of the present invention are shown in which electrolyte 58, membrane 60, gasket 66, and cover member 64 are illustrated. FIG. 3 is a cross-sectional view taken through line 3—3 of the partial assembly of FIG. 1, illustrating additional components, and FIG. 4 is a cross-sectional view taken through line 4—4 of the partial assembly of FIG. 2, also illustrating similar additional components. Specifically, provided atop reference electrode 50, counter electrode 52, and working electrode 54 or 154 in a preferred embodiment is electrolyte

58. Electrolyte 58 may be deposited in any manner so as to contact the above-noted electrodes without contacting conductive strips 34, 36, and 38 outside of the electrode region. That is, with reference to FIG. 1, electrolyte advantageously covers open printed region 48 entirely but does not extend outside of the region which is covered by dielectric layer 40 in the direction of the first end 41 of the substrate, that is, does not contact conductive strips 42, 44, or 46 outside of the region in which they are selectively exposed to define electrodes.

Electrolyte 58 preferably comprises a gel or solid-state electrolyte that swells to less than 2 times its dry volume when contacted with water or water vapor. More preferably, a solid-state electrolyte with a swell value of from about 5% to about 25%, most preferably from about 5% to about 10%, and which allows ion transport and does not allow electron transport, is utilized. A swell value of 10% is understood to indicate an increase in volume over a dry volume of an additional 10% when contacted with water or water vapor.

In a preferred embodiment, electrolyte 58 is a solid-state, chemically or physically cross-linked polymer that may be deposited from an organic solvent, that is hydrophilic in the solid state, that has an oxygen permeability of at least 3 Barrers, and that adheres well to surfaces to which it is applied, that is, dielectric 40 and electrodes 50, 52, and 54 or 154. Electrolyte 58 is also advantageously stable to any chemical species or reaction product generated during the operation of the sensor.

A Barrer is a unit of gas permeability defined by gas flux (at standard temperature and pressure) per unit time, multiplied by the thickness of the material, and divided by the area of the material and the pressure differential across the material in that area. The Barrer is defined by Equation 1.

$$1 \text{ Barrer} = 10^{-10} \times \frac{\text{flux}(\text{cm}^3) \times \text{thickness}(\text{cm})}{\text{area}(\text{cm}^2) \times \text{time}(s) \times P_{\text{diff}}(\text{cmHg})} \quad \text{(Eq. 1)}$$

Permeability values in Barrer units may be obtained according to the following method. A membrane to be tested is mounted so as to be contacted on a first side by flowing water having a partial pressure of oxygen equal to the partial pressure of oxygen in air, and contacted on a second side opposite the first side with flowing carrier gas, specifically nitrogen. The areas on the first and second sides of the membrane contacted by water and carrier gas, respectively, are of equal dimension. The carrier gas flowing past the membrane is analyzed for oxygen content using a potentiometric palladium oxygen sensor. Using measured values of oxygen flux as a function of time, the area of the membrane contacted by water on the first side and by carrier gas on the second, the thickness of the membrane, and the oxygen partial pressure differential across the membrane, permeability values in Barrer units according to Equation 1 are determined.

Preferably, electrolyte 58 is a solid-state ion transport electrolyte, specifically a cation or anion exchanger in its porotic form or exchanged with a metal ion. Such solid-state ion transport electrolytes are known in the art and suitable examples include a material sold under the trademark Nafion®, manufactured by DuPont and available from Aldrich Chemical Company of Milwaukee, Wis. In the preferred embodiment, lithium-exchanged Nafion is employed, but sodium-exchanged Nafion or porotic Nafion may also be utilized. Preparation of such exchanged Nafion is well-known to those of ordinary skill in the art. Certain Nafion compounds suitable for use as an electrolyte in the present invention are described in U.S. Pat. No. 4,536,274, referenced above.

Generally, electrolyte 58 is formed over the electrode region by applying lithium-exchanged Nafion in a solvent carrier to the electrodes and allowing the solvent to evaporate. It may be advantageous to heat the resultant residue for a period of time to completely evaporate the solvent carrier in a curing process. The electrolyte may be applied to the electrode area by spin-casting, a well-known technique in the art. Devices for carrying out spin-casting are readily commercially available.

Atop and completely covering electrolyte 58, semipermeable membrane 60 is provided in the preferred embodiments illustrated in FIGS. 3 and 4. Membrane 60 serves the purposes of protecting electrolyte 58 and electrodes 50, 52, and 54 or 154 from species such as metal ions, battery metals and liquid water which may be harmful to their intended operation, while passing species such as water vapor and oxygen necessary for sensor operation. Membrane 60 further serves the purpose of limiting passage of oxygen to the working electrode 54 or 154 so as to enhance the non-depleting nature of the sensor. A membrane suitable for use in the present invention has an oxygen permeability less than about 8 Barrers, preferably from about 0.1 to about 5 Barrers, and more preferably from about 0.2 to about 3 Barrers.

Membrane 60 is also preferably rapidly permeable to water vapor when Nafion is used as an electrolyte as, according to that embodiment, wetup of Nafion is necessary for its operation. Additionally, sensor stabilization is effected upon saturation of membrane 60 with water vapor. Thus, rapid permeability of membrane 60 to water vapor lessens the time to sensor stability in that regard. Preferably, membrane 60 has a water vapor permeability of at least 3 Barrers. Membrane 60 is also preferably impermeable to liquid water, and as a result impermeable to ions. A membrane deposited so as to have an impedance across the membrane, measured between the counter electrode on one side of the membrane and another electrode in saline solution on the other side thereof, of at least 12 megohms may be desirable in this regard. It is to be understood that the precise impedance across the membrane is not critical to the invention, but that impedance across the membrane may simply be used to evaluate materials which may be suitable for use in the present invention.

A membrane suitable for use in the present invention desirably has a degree of flexibility that will allow a solid-state electrolyte to swell and contract according to the values noted above, while adhering to adjacent sensor layers. Additionally, a membrane which is too brittle will delaminate from underlying sensor layers. The membrane also desirably possesses a durability sufficient to withstand pressure from an overlaying gasket according to a preferred embodiment of the present invention described below, while maintaining desirable microscopic physical and chemical characteristics.

Glass transition temperature may serve as an indicator of flexibility desirable in a material suitable for use as a membrane according to a preferred embodiment of the present invention. As is the case for membrane impedance, glass transition temperature of the membrane is not critical to the invention, but may be used as an evaluation method of selecting advantageous membranes. Material used for membrane fabrication should not have a glass transition temperature at or near the temperature at which the sensor normally operates, that is, 37° C. according to common blood analysis techniques. Preferably, membrane 60 is fabricated from a material having a glass transition temperature of from about −40° C. to about 110° C. but not at sensor operation temperature. More preferably, the glass transition temperature of membrane 60 is from about −15° C. to about 85° C. but not at sensor operation temperature.

Durometer values may indicate durability characteristics desirable in a material suitable for use as a membrane according to a preferred embodiment of the present invention. Material selected for fabrication of membrane 60 should have a Shore A hardness higher than that of the gasket, typically at least about 20, preferably at least about 50, and more preferably at least 70. The stated values are measured according to the well-known ASTM standard procedures.

As is the case with respect to other components of the inventive sensor as described above, initial evaluation of suitable membrane materials may be made on the basis of electrochemical investigation.

Specifically, in a sensor fabricated according to embodiments hereinabove described, the working and reference electrodes may be biased at a predetermined potential, and the sensor may be exposed to an aqueous solution to determine the water vapor permeability characteristic of the membrane. The membrane desirably passes water vapor rapidly, resulting in a current output which rapidly equilibrates to a steady-state reading, and remains relatively stable as a function of time.

The oxygen permeability of a membrane may also be tested according to the above-noted electrochemical methods, by exposing such a sensor to a solution having a known, predetermined $pO_2$, polarizing the sensor as described above, and measuring current output. A relatively low and stable output current may signify that the membrane operates, in concert with the small working electrode described above, to provide a substantially non oxygen-depleting sensor.

Additionally, the sensor may be exposed to a solution containing contaminants which, if they were to permeate the membrane, would adversely affect the electrolyte and/or electrodes or be electrochemically oxidized or reduced, giving false test result readings or no reading at all. Thus, exposure of the sensor to such a solution, and measurement of a polarogram during or following such exposure may determine permeability characteristics of a membrane. The potential longevity of a sensor may be tested by carrying out such electrochemical testing over a period of days and/or months where the sensor is stored exposed to such test solution and potentially biased. As noted above, according to a preferred embodiment of the present invention, any polarogram taken is advantageously free of significant peaks in a potential range in which electrochemical measurements are taken. In the preferred embodiment of the present invention, this is at approximately −0.800 volts, +/−0.300 volts vs. silver/silver chloride during its useful life.

An additional electrochemical test of significance is to expose such a sensor to a solution having a known, predetermined $pO_2$ for a long period of time, the sensor being polarized as described above, and observing the current output as a function of time. A desirable membrane oxygen permeability is such that, in a sensor having a small working electrode, exposure of the sensor to a sample having a $pO_2$ as low as that which will likely be measured and exhibits a current output which is as low as possible but high enough that $pO_2$ may be determined within an acceptable margin of error. A current output which is substantially free of long-term drift is also desirable. As used herein, "free of long-term drift" may be defined by current output, at a temperature stable to +/−0.1° C., at stable $pO_2$, and at a constant potential, which fluctuates less than +/−10% over a 24 hour period.

As noted, membrane 60 is desirably impermeable to water, permeable to water vapor and of limited permeability to oxygen. Therefore, the membrane is formulated to contain pendant groups which cause the polymer chains to interact in a way that imparts desirable physical characteristics to the membrane, and which provide the overall membrane composition with a desirable degree of polarity.

Generally, a membrane is water permeable if it contains a sufficient number of groups having a sufficient degree of polarity, especially if it contains groups which are amenable to hydrogen bonding. Generally, a membrane is gas permeable if it contains a sufficient degree of free volume. Free volume is decreased by such factors as polymer chain cross-linking and/or the presence of pendant groups in polymer chains that cause the polymer chains to bind to each other tightly. An additional consideration for gas permeability is the polarity of the particular gas molecule relative to the polarity of the membrane polymer. A polymer having greater numbers of groups having a high degree of polarity will generally be more permeable to a gas made up of polar molecules.

Typically, membrane 60 comprises a copolymer containing one or more types of pendant side groups selected, and occurring with a degree of frequency, so as to provide inter-chain dipole-dipole interactions that create a proper degree of free volume within the polymer and which provide the polymer with a proper degree of polarity. Additionally, such selection provides the polymer with desired overall mechanical characteristics such as a proper degree of flexibility. The pendant side group or groups are thus selected so as to have a polarity great enough to limit oxygen permeability to a level which provides for a non-oxygen-depleting oxygen sensor, and which allows for rapid water vapor transport, but which is low enough that the polymer remains hydrophilic, and is thus not permeable to ions. Providing a polymer for fabrication of a membrane that satisfies these requirements and is impermeable to carbon dioxide requires a balancing between polarity which decreases free volume, thus decreasing gas transport, and polarity which is attractive to carbon dioxide molecules.

According to one embodiment of the present invention, membrane 60 comprises a random or block copolymer comprising the polymerization product of at least one nitrile-containing monomer such as an alpha, beta-ethylenically unsaturated nitrile, for example acrylonitrile or methacrylonitrile and at least one conjugated diene monomer. Acrylonitrile is preferred for use as a nitrile-containing monomer according to a preferred embodiment. Non-limiting examples of conjugated dienes which may be used include 1,3-butadiene; isoprene; 2,3-dimethyl-1,3-butadiene; 1,3-pentadiene; 3-butyl-1,3-octadiene and others well-known to those of ordinary skill in the art, and mixtures thereof, with 1,3-butadiene being preferred.

As used herein, the term "polymerization product" refers to a product of standard polymerization methods such as anionic polymerization, cationic polymerization, free radical polymerization, coordination polymerization, and the like.

Preferably, a random copolymer comprising the above-noted polymerization products is formulated, in which the nitrile-containing monomer is added in an amount of from about 5% to about 80%, preferably from about 15% to about 55%, and more preferably from about 30% to about 40% by weight, based on the weight of the polymerization product. While a random copolymer is generally selected and formulated, a block copolymer comprising polymerized blocks of nitrile-containing monomers and conjugated diene monomers may be selected and formulated.

A suitable membrane material desirably comprises polymer chains which are not cross-linked or, if cross-linked to any degree, maintain a desirable glass transition temperature and a desirable oxygen permeability.

A polymer for use in fabricating a semipermeable membrane in accordance with one embodiment of the present invention is a random acrylonitrile-butadiene copolymer containing acrylonitrile in an amount of from about 5% to about 80% by weight, preferably from about 15% to about 65% by weight, more preferably from about 30% to about 50% by weight. The acrylonitrile may be isotactic, syndiotactic, or atactic. Generally, the acrylonitrile is atactic. The butadiene may be of a various degree of isometric purity. Typically, the butadiene group is not pure isomerically but is a mixture of cis and trans-monomers and includes pendant vinyl groups. The butadiene group may be saturated or unsaturated, and is generally substantially unsaturated in a preferred embodiment.

According to another embodiment, membrane 60 comprises the above-described nitrile/conjugated diene copolymer to which the polymerization product of a vinyl halide, a vinylidene halide, either of the two copolymerized with a nitrile-containing monomer, or a combination of any of the above is added in an amount of from about 1 to about 70% by weight, based on the weight of the overall membrane composition, preferably in an amount of from about 15% to about 50% by weight, and more preferably in an amount of from about 30% to about 40%. Preferably isotactic, syndiotactic or atactic polyvinyl chloride or a random copolymer of polyvinylidene chloride and acrylonitrile in which the polyvinylidene chloride is added in an amount of from about 40% to about 95% by weight, preferably from about 60% to about 90%, and more preferably about 80% by weight, based on the weight of the polyvinylidene chloride/acrylonitrile copolymer, are selected and added. The addition of these species to the nitrile/conjugated diene polymer has the effect of lowering the oxygen permeability of the membrane, and resultant normalized current response of the sensor. Additionally, addition of these species typically provide a membrane which is more durable than a nitrile/conjugated diene polymer alone, which is advantageous in the fabrication of a sensor having a sample chamber constructed on the membrane, that is, a sample chamber defined in part by the membrane, and constructed so as to expose the membrane, above the electrode area, to samples to be analyzed. Additionally, addition of these species may enhance sensor longevity. Thus, the membrane may be tailored with respect to oxygen permeability and durability by adjusting the composition ratio of the polymer blend.

The polyvinyl chloride and/or polyvinylidene chloride/acrylonitrile copolymer is preferably incorporated in the nitrile/conjugated diene copolymer to form a mixed or blended polymer composition by conventional blending technique such as cosolvation in a mutual solvent, standard blending processes, and the like. In a preferred embodiment, cosolvation is employed.

One of the advantages of cosolvation of a polyvinylidene chloride/acrylonitrile copolymer with a nitrile/conjugated diene copolymer is that the miscibility of the two copolymers in the mixture, and thus the homogeneity of the mixture, is increased.

According to another embodiment, membrane 60 is made from a polymer or copolymer of an ester of an alpha, beta-ethylenically unsaturated carboxylic acid, for example a member of the group of alkyl acrylates or methacrylates. Optionally, there may be included in the copolymer one or more monomers selected from the group including vinyl acetate, styrene, vinyl toluene, vinyl chloride, vinylidine chloride, and an alpha, beta-mono-ethylenically unsaturated acid or an amine-containing monomer. Typically, membrane 60 comprises the polymerization product of at least one acrylate monomer, that is, a monomer having the formula $CH_2=C(R_1)(COOR_2)$, where $R_1$ and $R_2$ are each selected from the group consisting of hydrogen, hydrocarbon groups, and alcohol groups and $R_1$ and $R_2$ can be the same or different. Hydrocarbon groups such as hydrogen, alkyl, alkenyl, alkynyl, cycloalkyl, aryl, alkaryl, aralkyl, and the like may be selected. As used herein, the terms "hydrocarbon", "alkyl", "cycloalkyl" and similar hydrocarbon terminology is meant to include alcohols and hydrogen, although specific reference to the inclusion of hydrogen and/or alcohols is frequently made herein. Examples of such groups are methyl, propenyl, ethynyl, cyclohexyl, phenyl, tolyl, benzyl, hydroxyethyl and the like. $R_1$ is preferably selected from groups including hydrogen and the general class of lower alkyl compounds such as methyl, ethyl, or the like.

$R_2$ is preferably an alkyl group, preferably having 1 to 24 carbon atoms, most preferably 1 to 18 carbon atoms; and alkenyl group, preferably having 2 to 4 carbon atoms; an aminoalkyl group, preferably having 1 to 8 carbon atoms, and optionally substituted on the nitrogen atom with one or, preferably two alkyl groups, preferably having 1 to 4 carbon atoms; an alkyl group, preferably having 1 to 4 carbon atoms, having a five or six-membered heterocyclic ring as a substituent; an allyloxyalkyl group, preferably having up to 12 carbon atoms; an alkoxyalkyl group, preferably having a total of 2 to 12 carbon atoms; an aryloxyalkyl group, preferably having 7 to 12 carbon atoms; an aralkyl group, preferably having up to 10 carbon atoms; or a similar alkyl or aralkyl group having substituents which will not interfere with the polymerization of the ester.

That is, homopolymers and copolymers advantageously used for membrane 60 may include esters selected from the group consisting of $(C_1-C_{24})$alkyl esters of acrylic acid, preferably a $(C_1-C_4)$alkyl acrylate, di$(C_1-C_4)$alkylamino$(C_2-C_4)$alkyl esters of acrylic acid, $(C_1-C_8)$alkoxyalkyl esters of acrylic acid, $(C_6-C_{10})$aryloxyalkyl esters of acrylic acid, $(C_7-C_{10})$aralkoxyalkyl esters of acrylic acid, and $(C_7-C_{10})$aralkyl esters of acrylic acid, The copolymers of this invention include polymers in which more than one monomer is selected from a given group, for instance, the case where the polymer is a copolymer of at least two $(C_1-C_{24})$alkyl acrylates. Other copolymers of the invention comprise monomers which may or may not be acrylates, such as copolymers of at least one $(C_1-C_{24})$alkyl acrylate and at least one other copolymerizable ethylenically-unsaturated monomer. This copolymerizable monomer may be acrylonitrile or dimethylaminoethyl acrylate, preferably when the alkyl acrylate is a $(C_1-C_4)$alkyl acrylate.

Among the esters embraced by the formula $CH_2=C(R_1)(COOR_2)$ which are suitable monomers are unsubstituted alkyl acrylates, in which the alkyl group can have branched or straight-chain, cyclic or acyclic spatial configurations, such as methyl acrylate, ethyl acrylate, propyl, isopropyl and cyclopropyl acrylates, isobutyl, t-butyl, n-butyl and cyclobutyl acrylates, pentyl and cyclopentyl acrylates, hexyl and cyclohexyl acrylates, heptyl and cycloheptyl acrylates, octyl, acrylates, including 2-ethylhexyl acrylate, nonyl acrylates, decyl acrylates, undecyl alcrylates, lauryl acrylates, myristyl acrylates, cetyl acrylates, stearyl acrylates, and the like; aralkyl acrylates, such as phenylethyl acrylates, phenylpropyl acrylates, and the like; aralkyl acrylates, in which the aryl group is substituted with alkyl groups, halogen atoms, alkoxy groups, nitro groups, or similar substituents which will not interfere with the polymerization reaction; alkenyl acrylates, such as allyl acrylate, and the like; aminoalkyl acrylates, such as dimethylaminoethyl acrylate, phenylaminoethyl acrylates, t-butylaminoethyl acrylates, dimethylaminobutyl acrylates, diethylaminoethyl acrylate, and the like; alkyl acrylates having a heterocyclic group as a substituent on the alkyl group, such as morpholinoalkyl acrylates, oxazolidinylalkyl acrylates, piperidinodalkyl acrylates, dioxolanylalkyl acrylates, i.e., ketals and acetals of glyceryl acrylate, and the like; iminoalkyl acrylates, such as ketiminoalkyl acrylates and aldiminoalkyl acrylates; alkoxyalkyl, aryloxyalkyl, and aralkoxyalkyl acrylates, such as methoxyethyl acrylate, ethoxyethyl acrylate, butoxyethyl acrylates, hexyloxypropyl acrylates, ethoxypropyl acrylates, propoxybutyl acrylates, hexloxyhexyl acrylates, phenoxyethyl acrylates, benzyloxyethyl acrylates, and the like; and allyloxyalkyl acrylates, such as allyloxyethyl acrylate, allyloxyethoxyethyl acrylate, allyloxypropyl acrylate, and the like. Bis acrylate esters of diols, such as the diester of 1,4-butanediol and acrylic acid, can also be used. Other esters of acrylic acid which do not contain substituents which would interfere with the polymerization of these esters are also suitable.

$R_2$ is preferably selected from linear, branched and cyclic hydrocarbons and alcohols of from 1 to 20 carbon atoms. $R_1$ and $R_2$ may each individually, or both, comprise groups having substituted for non-substituted hydrocarbons and may comprise heteroatoms. Preferably, any substitution results in non-reactive groups.

A preferred class of polymer mixtures suitable for fabrication of membrane 60 includes the above-noted polymer or copolymer of at least one acrylate monomer which may be polymerized with at least one additional monomer. A non-limiting list of suitable additional monomers which may be polymerized with one or more acrylates to form polymerization products include at least one nitrile-containing monomer; the polymerization product of at least one monomer having the formula $CH_2=C(R_1)(CONR_2R_3)$, where $R_1$, $R_2$, and $R_3$ are each selected from the group consisting of hydrogen, hydrocarbon groups, and alcohol groups and $R_1$, $R_2$, and $R_3$ can be the same or different; and the polymerization product of at least one monomer having the formula $CH_2=C(R_1)(OCOR_2)$, where $R_1$ and $R_2$ are each selected from the group consisting of hydrogen, hydrocarbon groups, and alcohol groups and $R_1$ and $R_2$ can be the same or different.

According to one preferred class of polymer mixtures suitable for formulation of membrane 60, a mixture is selected which includes the polymerization product of at least one monomer having the formula $CH_2=C(R_1)(COOR_2)$ where $R_1$ is selected from the group consisting of hydrogen and lower alkyl groups, $R_2$ is selected from the group consisting of linear, branched and cyclic hydrocarbons and alcohols of from 1 to 20 carbon atoms, $R_1$ and $R_2$ being the same or different, present in an amount of from about 20% to about 80% by weight based on the weight of the membrane, preferably from about 40% to about 60% by weight. Also included is the polymerization product of at least one nitrile-containing monomer present in an amount of from about 15% to about 80%, preferably from about 20% to about 30% by weight, and the polymerization product of either a monomer having the formula $CH_2=C(R_1)(OCOR_2)$ where $R_1$ and $R_2$ are each selected from the group consisting of hydrogen, lower alkyl groups and lower alcohols and $R_1$ and $R_2$ can be the same or different, or a monomer having the formula $CH_2=C(R_1)(CONR_2R_3)$ where $R_1$, $R_2$, and $R_3$ are each selected from the group consisting of hydrogen and lower alkyl groups and $R_1$, $R_2$, and $R_3$ can be the same or different. A combination of the latter two monomers may be added, and in a preferred embodiment the monomer having the formula $CH_2=C(R_1)(OCOR_2)$, where $R_1$ and $R_2$ are each selected from the group consisting of hydrogen, lower alkyl groups and lower alcohols and $R_1$ and $R_2$ can be the same or different and is present in an amount of from about 15% to about 30% by weight.

Specific examples of monomers suitable for polymerization to form a membrane copolymer composition according to this embodiment of the present invention include, but are not limited to: acrylonitrile, 2-ethylhexylmethacrylate, methylmethacrylate, dodecylmethacrylate, vinylacetate, cyclohexylmethacrylate, 2-hydroxypropylmethacrylate, and acrylamide.

A random copolymer of components described above may be formulated, or a block copolymer comprising blocks having molecular weights of from about 10,000 to about 100,000 of the above-described monomers may be formulated. Preferably, the membrane is formulated from a random copolymer of the above-noted monomers. The copolymer may be cross-linked, but is preferably not cross-linked or cross-linked to a limited extent so as to maintain adequate free volume and flexibility.

The polymer membrane compositions of the invention may be produced by any convenient polymerization method, such as anionic polymerization or free-radical polymerization, or the like.

According to another embodiment, membrane 60 comprises a polyimide compound, which may be a homopolyimide, or a copolymer comprising imide functionalities and other groups. Preferably, according to this embodiment, membrane 60 comprises aromatic polyimides of aromatic diamines which are substituted in the nucleus by alkyl, and aromatic diamines which carry sulfonic acid groups which may be in salt form, and aromatic tetracarboxylic acids. In a preferred embodiment, membrane 60 comprises aromatic copolyimides of aromatic tetracarboxylic acids and tricarboxylic or aromatic tricarboxylic acids and a first aromatic diamine and a second aromatic diamine which carries— $SO_3H$— groups in salt form, said first and/or said second diamine being $C_1$–$C_4$alkyl-substituted in both ortho-positions to at least one amino group. Such materials are described in U.S. Pat. No. 5,145,940, incorporated herein by reference.

According to yet another embodiment, membrane 60 may comprise a polyamide, copolyamide or copolyimide-amide compound, preferably aromatic copolyamides and copolyimide-amides of two aromatic diamines, one of which may contain sulfonic acid groups. Such compounds are disclosed in European Patent Application No. EP-A-0473541, incorporated herein by reference.

According to this embodiment, membrane 60 preferably comprises a copolyamide or copolyimide-amide of (a) at least one aromatic dicarboxylic acid radical of 8 to 20 carbon atoms and/or (b) at least one trivalent aromatic tricarboxylic acid radical of 9 to 20 carbon atoms, each of which radicals is unsubstituted or substituted by halogen, nitro, $C_1$–$C_4$alkyl or $C_1$–$C_4$alkoxy, (c) at least one first divalent and/or trivalent mononuclear or binuclear aromatic diamine radical and (d)

at least one second divalent and/or trivalent aromatic mononuclear or binuclear diamine radical containing at least one —$SO_3M$ group, each of which radicals is unsubstituted or substituted by halogen or $C_1$–$C_4$alkyl, and M is $H^+$, a monoto trivalent metal cation, $NH_4^+$ or an organic ammonium cation of 1 to 30 carbon atoms. When membrane 60 comprises a copolyamide or copolyimide-amide containing —$SO_3M$ groups, such groups are desirably present to an extent less than that which would cause the membrane to be water permeable, and thus ion permeable.

M in the $SO_3M$ group as ammonium cation may be $NH_4^+$ or an ammonium cation of a primary, secondary or tertiary open-chain amine containing preferably 1 to 24 carbon atoms, most preferably 1 to 16 carbon atoms, or an ammonium cation of a monocyclic or bicyclic secondary or tertiary amine or of a tricyclic tertiary amine containing preferably 4 to 12 carbon atoms.

M as a metal cation is selected in accordance with the teachings herein regarding species which may not be desirable for incorporation into components of the sensor 30. That is, mobile battery metals present in the membrane are undesirable. With this in mind, M as a metal cation is desirably a mono to trivalent cation of metals of the main groups and subgroups, of the transition metals and of the noble metals. Mono or divalent cations are preferred.

In a preferred embodiment of the invention, M is $H^+$, $NH_4^+$, an alkali metal cation or a primary, secondary, tertiary or quaternary ammonium cation of 1 to 24 carbon atoms.

The copolyamide or copolyimide-amide preferably contains 60 to 95 mol %, most preferably 75 to 95 mol %, of diamine radicals (c) and 5 to 40 mol %, most preferably 5 to 15 mol % of diamine radicals (d), based on said diamine radicals. The inherent viscosity of the copolyamides, copolyamide-imides or of the copolymers can be from 0.2 to 3.0 dl/g, preferably 0.3 to 2.0 dl/g and, most preferably, 0.3 to 1.2 dl/g.

Figure 5:
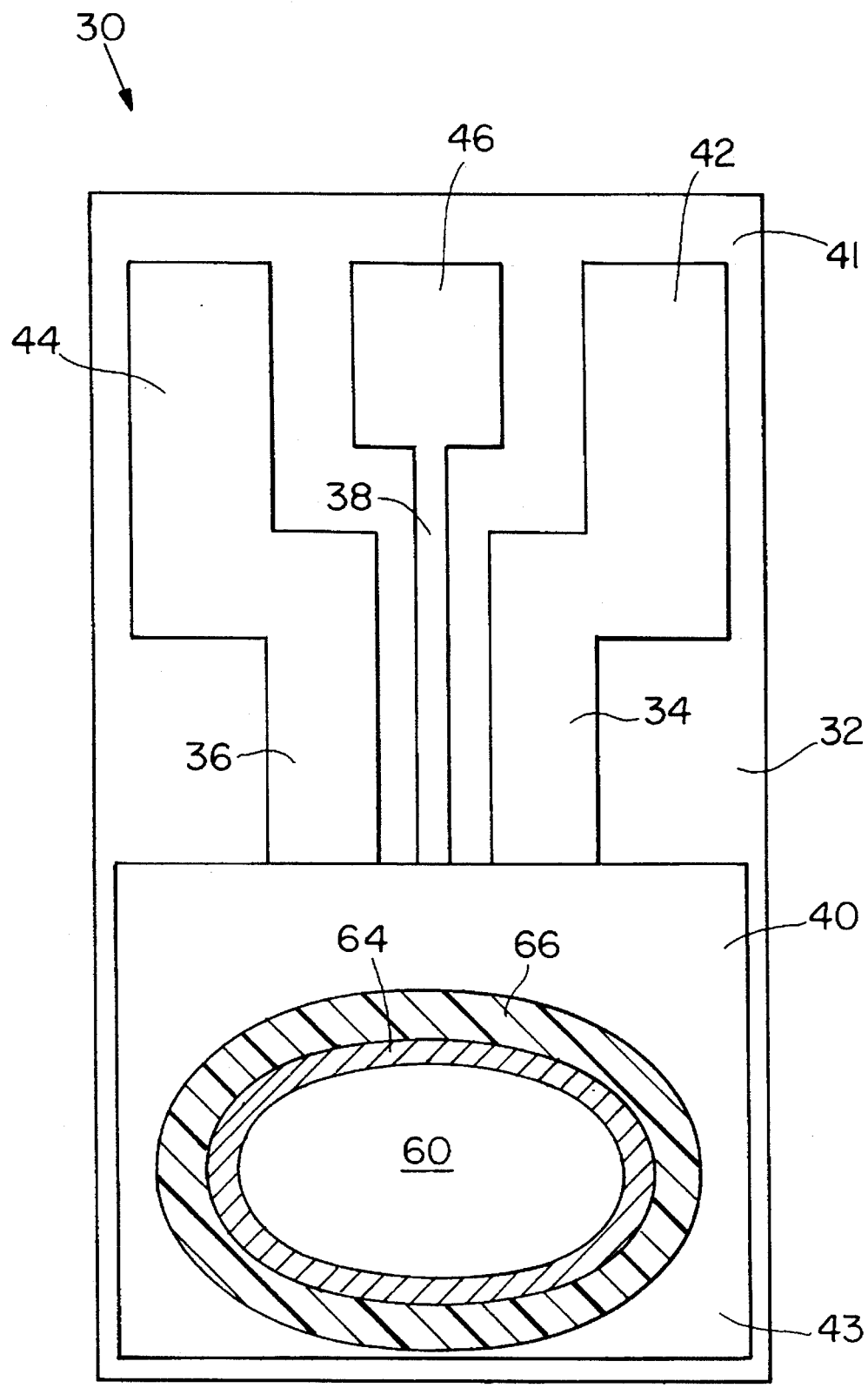
FIG. 5 is a cross-sectional view through line 5—5 of FIGS. 3 or 4 showing this view of the embodiments of FIGS. 3 and 4 to be identical.

Referring now to FIGS. 3–5, a preferred embodiment of the present invention is illustrated in which a sample chamber 62 is provided above the electrode region at end 43 of sensor 30 or 130. Chamber 62 is defined by a substantially oval recessed region of cover member 64, the perimeter of which is held firmly against gasket 66 at seal 67, which is in turn held firmly against dielectric layer 60 at seal 69. Thus, sample chamber 62 is defined by dielectric layer 60, gasket 66 and cover member 64. At least one passage 68, and preferably two passages 68 and 70, serving as inlet and outlet channels, respectively, are formed in cover member 64 to allow passage of a fluid sample such as blood into and out of the sample chamber 62 of the sensor. In the embodiment illustrated, channels 68 and 70 pass through cover member 64. However, channels may be formed in any manner so as to provide a passageway through which a fluid sample could reach sample chamber 62. For example, channels could be formed in gasket 66 between gasket 66 and cover member 64, between dielectric 60 and gasket 66, etc.

Cover member 64 may be fabricated from any material that is unreactive with a sample which passes into sample chamber 62 during analysis, as for example, glass, ceramic, stainless steel, or plastic. Preferably, plastic is used in the formation of cover member 64.

Gasket 66 is advantageously formulated from a material which, when held firmly between cover member 64 and dielectric layer 60, forms a seal around sample chamber 62 through which the passage of fluid and gas is substantially barred such that testing may be carried out for a period of at least 2 days under normal sensor operation. "Normal sensor operation", as used herein, refers to operation in which a sensor is exposed to at least 10 blood samples a day and/or calibrators, quality control solutions, controls, proficiency testing solutions, calibration verification materials, and the like while continuously polarized at 37° C. so as to measure a current response, or operation in which a sensor is exposed to a blood-mimicing saline solution and is polarized at measuring potential, continuously, as described above. Additionally, normal sensor operation may be defined by the test protocol described below in Example 58. In actual use of a sensor according to the present invention, the sensor would not be polarized at a measuring potential continuously. Therefore, it is to be understood that "normal sensor operation" may refer to a prescribed longevity or durability measurement or both. The term "blood", as used herein, refers to whole blood containing anticoagulants, plasma, serum or other blood solutions or suspensions.

Typically, gasket 66 is formulated from a durable organic polymer which does not creep or flow when stressed, which has a low durometer rating so that damage to membrane 60 is minimized or eliminated, which is gas impermeable, and which may be slightly hygroscopic and thus may swell slightly in the presence of solution containing water, to form efficient seals 67 and 69.

Preferably, material used in the fabrication of gasket 66 has a hardness of between 10 and 100 on the Shore A scale, more preferably a hardness of from about 40 to about 70 on the Shore A scale, and most preferably a hardness of from about 45 to about 55 on the Shore A scale.

Gasket 66 desirably has sub-microscopic properties which make it gas impermeable, and is thus preferably formulated from a precursor having a sufficient degree of unsaturated carbon-carbon bonds to form a sufficiently highly cross-linked polymer compound when cured, or have other means of attaining such a degree of cross-linking. Specifically, the material from which gasket 66 is made has an oxygen permeability of less than about 20 Barrers, preferably less than about 5 Barrers, and most preferably less than about 0.5 Barrers.

As gasket 66 is typically an organic polymer, it is fabricated so as not to contain a substantial amount of any mobile extractable materials such as plasticizers which may leach into semipermeable membrane 60. Such leaching of extractables can affect the microscopic physical properties of the membrane, disadvantageously effecting a change in the above-noted advantageous permeability characteristics of the membrane. This is an especially notable consideration with respect to sensors designed for long-term use, on the order of for example days or months and to sensors operating with small test sample volumes. Additionally, as is the case for other sensor components as described above, it is important that material selected for formation of gasket 66 be free of any species which could migrate into a sample in chamber 62, affecting electrochemical measurements, and/or destroying sensor components. Material used in the formation of gasket 66 is preferably selected to be essentially free of mobile transition and main group metals, especially battery metals such as iron, cobalt, nickel, lead, copper, extractables, and species such as sulfides which are deleterious to preferred electrode materials, such that electrochemical response is not affected over long-term sensor use, specifically for at least 2 days of normal sensor operation.

Gasket 66 is typically formed from a highly cross-linked elastomeric compound. Any elastomeric material which meets all the purity and physical requirements listed above may serve. A preferred embodiment of this material is composed of a copolymer of an epoxy compound and a small amount of another monomer which provides sites of unsaturation in the copolymer. The second monomer may be added in amounts to give from about 0.1 to about 20% crosslinking upon cure (1% crosslinking would indicate that, on the average, 1 out of every 100 monomers in a chain would be a point at which the elastomer is crosslinked). A more preferred degree of crosslinking would be from about 1 to about 15% and the optimum performance would be obtained in a material with from about 6 to about 14% crosslinking.

A more preferred embodiment is obtained when the epoxy compound is composed of epichlorohydrin and the second monomer is allyl glycidyl ether. The sites of unsaturation provided by the second monomer allow the material to be crosslinked to form an elastomer using any convenient free radical mechanism, for example via peroxide.

In order to provide the proper amount of swelling in aqueous or blood based solutions, a third monomer may be added to the prepolymer mixture. Examples of suitable monomers include allyl alcohol, crotyl alcohol, methylvinyl carbinol, cinnamyl alcohol, ethylene glycol, propylene glycol, 1,3-propanediol, glycerol, pentaerythritol, acrylamides, acrylic monomers, and the like.

In addition, it may be necessary to add processing aids to the prepolymer. These include alkali stearates, alkali oxides, and the like.

A partial list of curing agents include 2,5-bis (t-butylperoxy)-2,5-dimethylhexane, dicumyl peroxide, di-tert-butyl peroxide, and dilaurate peroxide. Any peroxide curing agent which generates free radicals at temperatures below 180° C. and can be dispersed in the prepolymer may be used as the curing agent.

A polyfunctional monomer may be used to facilitate the crosslinking reaction during the cure. This monomer should be similar to the unsaturated sites in the prepolymer to react easily with these sites. Examples include 2-ethyl-2-hydroxymethyl-1,3-propanediol trimethacrylate, diethylene glycol diacrylate, 1,4-butanediol diacrylate, divinyl benzene, glyceryl propoxy triacrylate, and dipentaerythritol monohydroxypentaacrylate. The preferred monomer is 2-ethyl-2-hydroxymethyl-1,3-propanediol trimethacrylate.

This polyfunctional monomer should be added in an equivalent amount to the unsaturation sites in the prepolymer. Equivalence in this case meaning the same number of reactive sites are in the prepolymer as are found in the polyfunctional monomer. For example, if the polyfunctional monomer is trifunctional, there should be one of these monomers for every three sites of unsaturation in the prepolymer.

Specific epoxy polymerization products preferred for use as gasket materials include: the polymerization product of an epichlorohydrin homopolymer having a molecular weight of from about 2,000 to about 1,000,000 and alkyl glycidyl ether, the ratio of the epichlorohydrin homopolymer to alkyl glycidyl ether being from about 0.5% to about 20% by weight, available under the trademark Grechon 1100 from Zeon Chemicals of Kolling Meadow, Ill.; 2-ethyl-2-hydroxymethyl-1,3-propanediol trimethacrylate, available as catalog number SR-350 from Sartomer Company of Exton, Pa.; potassium stearate; calcium oxide; (2,5-bis(t-butylperoxy)-2,5-dimethylhexane, available under the trademark Varox DBPH-50 from R. T. Vanderbilt of Norwalk, Conn.; and stearic acid.

According to the present invention, a sample chamber 62 of any size, including a very large chamber, may be fabricated. Fabrication of a large sample chamber may be advantageous in some circumstances. As noted above, however, in the field of electrochemical analysis of blood, it is commonly desirable to perform as many analyses as possible on a very small volume of blood. Thus, according to a preferred embodiment of the present invention, it is desirable to fabricate sensor 30 or 130 with a sample chamber 62 that is as small as possible. Using the novel materials and methods of the present invention, a sample chamber having a volume of less than 10 μl, preferably from about 0.8 to about 3 ml, and more preferably from about 1 to about 2 μl, which sensor may effectively be utilized for a period of many days or months, is possible.

A variety of shapes and configurations of components comprising sensor 30 or 130 may be achieved using the well-known thick and thin-film techniques. U.S. Pat. No. 4,571,292, which is incorporated by reference herein, discloses a variety of electrode configurations that may be advantageous in some circumstances. Variation of configuration in accordance with these references and other configurations easily achieved by one of ordinary skill in the art are within the scope of the present invention.

With this in mind, and with reference to FIGS. 1–5, the following non-limiting preferred dimensional specifications of a sensor fabricated in accordance with a preferred embodiment of the present invention are given.

Substrate 32 may be of any of a variety of shapes and sizes. According to one specific preferred embodiment of the invention substrate 32 is from about 0.5 to about 2 cm long, preferably about 1.2 cm long and from about 0.2 to about 1 cm wide, preferably about 0.5 cm wide. According to another specific preferred embodiment, substrate 32 is from about 3.5 to about 7 cm long, preferably about 5.0 cm long and from about 1.5 to about 3.5 cm wide, preferably about 2.5 cm wide. Substrate 32 is from about 0.1 to about 0.5 mm thick, preferably about 0.25 mm thick. Conductive strips 34, 36, and 38 are deposited each in a thickness of from about 0.002 to about 0.04 mm thick, preferably about 0.013 mm thick. Conductive strips 34 and 36, at end 43 of the sensor, are from about 0.5 to about 3.0 mm wide, preferably about 1.25 mm wide. Conductive strip 38, at end 43 of the sensor, is from about 0.02 to about 0.4 mm wide, preferably about 0.10 mm wide.

Dielectric layer 40 is preferably deposited in a thickness of from about 0.004 to about 0.05 mm thick, preferably about 0.019 mm thick. Thickness values are given after firing or curing. Although dielectric layer 40 abuts edges of conductive strips 34 and 36 in the embodiments illustrated in FIGS. 1–4, such need not be the case. The open printed region 48 defined by dielectric layer 40 preferably includes a gap 49 having a width of from about 0.02 to about 0.4, preferably about 0.10 mm.

Thus, the exposed surface area of reference electrode 50 and counter electrode 52 is about 1.6 mm$^2$ for each, and working electrode 54 has a surface area of about 0.01 mm$^2$, according to the embodiment illustrated in FIG. 1. These exposed surface area dimensional specifications do not take into consideration surface area due to the edges of the electrodes, defined by the thickness of the electrodes as deposited. Such edge dimensions are minimal relative to the overall electrode areas. However, the exposed surface area specifications are thus somewhat approximate.

According to the embodiment illustrated in FIGS. 2 and 4, in which a laser or a needle is used to form a hole or opening 56 in dielectric layer 40 exposing working electrode 154, hole or opening 56 may be formed having a diameter of as small as 0.5 mm, and is typically formed in any size up to approximately 100 mm in diameter. Typically, hole or opening 56 has a diameter of about 3 mm. Thus, the surface area of working electrode 154 may be from about $2\times10^{-13}$ m$^2$ to about $8\times10^{-9}$ m$^2$.

Polymer electrolyte 58 is typically spun-cast over the electrodes and dielectric to a thickness of from about 0.001 mm to about 0.050 mm, preferably from about 0.005 mm to about 0.010 mm thick. During the spin-casting process, regions of conductive strips 34, 36 and 38 that are not covered by dielectric 40, and contact pads 42, 44 and 46, are masked. Accordingly to an alternate method, polymer electrolyte 58 may be deposited in a dropwise manner from an X-Y-Z table such as that described above, to control placement.

Thereover, cover membrane 60 is deposited, preferably spun-cast to a thickness from about 0.005 mm to about 0.050 mm, preferably from about 0.010 mm to about 0.020 mm. As is the case for polymer electrolyte 58, cover membrane 60 may alternately be deposited in a dropwise manner from an X-Y-Z table. The dimensions of gasket 66 and cover member 64 are such that a sample chamber 62 has a width of from about 1 to about 10 mm, preferably from about 3 to about 4 mm and a height of from about 0.3 to about 2.0 mm, preferably from about 0.6 to about 0.9 mm is defined. As noted, chamber 62 has a preferred volume of from about 1 to about 2 μl.

In the following examples, a Faraday cage was used when radio frequency signal interference was noted. All fluid samples were held at a constant temperature of at or near 37° C., physiological temperature.

The following examples are intended to illustrate the benefits of the present invention, but do not exemplify the full scope of the invention. For example, although the thick-film technique is exclusively exemplified, it is to be understood that the thin-film technique may be selected; although three-electrode sensors are exclusively exemplified, two-electrode sensors may be fabricated. It is also noted that many features of the invention, for example the novel membrane and gasket compositions and the chamber construction and working electrode formation, are not limited to use in a planar, solid-state oxygen sensor. Additionally, as noted above, the specific shape and arrangement of the electrodes and conductive strips of the present invention may be significantly altered, such alteration being within the scope of the present invention. Use of components of the present invention in a non-planar sensor, and/or one having a liquid electrolyte may be advantageous, as well as use in sensors constructed to detect a variety of analytes. Non-sensor use of the membranes, gaskets, and chamber, and/or electrode formation described herein is also within the scope of the present invention. These and other modifications and their equivalents are understood to be within the scope of the present inventions.

EXAMPLE 1

Referring now to FIGS. 1–5, a partial assembly of a planar oxygen sensor 30 having substrate layer 32 and conductive metal strips 42, 44, and 46 was fabricated in accordance with a method of the present invention on a 2.5 cm by 5 cm electrically non-conducting substrate 32 comprising approximately 96% alumina and approximately 4% glass binder, available from Coors Ceramic Company, Grand Junction, Colo. Using the thick-film technique, conductive strip 34 was fabricated by silk-screening a 0.01 mm emulsion silver paste available as part number 3571 UF from Metech Company of Elverson, Pa., onto the substrate. A 325 mesh screen made of 1.1 mil diameter SS wire was used. Subsequently, a 0.4 mil emulsion silver/silver chloride paste, available as part number PC 10299 from Metech, was silk-screened over a portion of conductive strip 34 at end 43 of sensor 30, covering an area of conductive strip 34 at least as large as, and preferably larger than, the area of conductive strip 34 to be exposed by open printed region 48 to define reference electrode 50. A screen similar to that described above was used. For purposes of clarity, in FIGS. 3 and 4 reference electrode 50, created in accordance with this example as a silver/silver chloride electrode, is illustrated as a single metal layer. In this and subsequent examples, a BTU 7 zone belt furnace with a 3 zone dryer, from Fast Fire of Billerica, Mass., was used in firing pastes. Firing was carried out per manufacturer's recommendations, ramped to the peak conditions listed below. Conductive strip 34 was fired at 850° C. for 10 minutes. Subsequently, a gold paste, available as part number JM 1301 from Johnson-Matthey, of West Deptford, N.J. was silk-screened onto substrate 32 to define conductive strip 36. A similar emulsion and screening technique was employed. The paste was fired at 850° C. for 10 minutes. Then, a 0.2 mil emulsion high-purity platinum paste, as described above and available as part number PC 10208 from Metech, was silk-screened onto substrate 32 to define conductive strip 38. A 400 mesh screen made of 0.9 mil diameter SS wire was used. The paste was fired at 870° C. for 13 minutes.

Substrate 32 was 0.25 mm thick. Conductive strips 34 and 36 were deposited on substrate 32 so as to be 1.25 mm wide at end 43 of substrate 32, and 0.014 mm thick. Conductive strip 38 was deposited so as to be 0.1 mm wide at end 43 of substrate 32. At end 41 of substrate 32, where conductive strips 34, 36, and 38 define contact pads 42, 44, and 46, respectively, these strips were deposited so as to 0.25 cm wide. Dimensions given in this and subsequent examples are those after firing, and are approximate.

EXAMPLE 2

A partial assembly of a planar oxygen sensor 30 having substrate layer 32 and conductive metal strips 42, 44, and 46 was fabricated in accordance with Example 1 with the following exceptions. Substrate 32 was approximately 11 mm long and approximately 4.5 mm wide. Contact pads 42, 44, and 46 were each approximately 0.5 mm wide. Contact pads 42, 44, and 46 were each fabricated from gold, and portions of conductive strips 34, 36, and 38 connecting the contact pads with the electrodes were fabricated from gold.

EXAMPLE 3

Referring now specifically to FIGS. 1 and 3, onto a partial assembly of each of the sensors fabricated in accordance with Examples 1 and 2, a ceramic dielectric 40, available as part number 9615 from DuPont was silk-screened as a 0.6 mil emulsion over a large portion of end 43 of sensor 30. A 325 mesh screen made of 1.1 mil diameter SS wire was used. The silk-screening was effected in a manner so as to leave an open printed region 48, exposing areas of conductive strips 34 and 36 of 1.25 mm by 1.25 mm; an area of conductive strip 38 of 0.1 mm by 0.1 mm; and areas between the exposed areas of the conductive strips. Thus, open printed region 48 exposes portions of conductive strips 34, 36, and 38 and defines reference, counter and working electrodes 50, 52, and 54. Dielectric 40 was fired per manufacturer's recommendation, ramped to a 750° C., 8 minute peak to give a thickness of about 0.019 mm. The area of sensor covered by dielectric layer 40, extending from open printed region 48, is not critical to the invention. The area need only extend over conductive strips 34, 36, and 38 away from open printed region 48 to points that are not addressed by any electrolyte, as described below.

EXAMPLE 4

Referring now specifically to FIGS. 2 and 4, onto a partial assembly of each of the sensors fabricated in accordance with Examples 1 and 2, a sensor 130 was fabricated in accordance with Example 3, with the exception that a polymer dielectric 40, specifically an unsaturated polyester resin containing phthalic anhydride, maleic anhydride, glycols and unsaturated oils, available as part number ESL 240SB clear from Electro Science Laboratories of King of Prussia, Pa., was deposited so as to completely cover conductive strip 38 in the sensor region at end 43 of sensor 30. A 325 mesh screen made of 1.1 mil diameter SS wire was used. Polymer dielectric 40 was cured at 200° C. for 2 hours in a curing oven available from Despatch, Inc. of Minneapolis, Minn. Dielectric 40 was deposited so as to define a thickness of about 0.021 mm after curing, Thereafter, sensor 130 was positioned on an X-Y-Z table, available as model AUTOMOVE 302/201 from Asymtek Corporation of Carlsbad, Calif. The X-Y-Z table was positioned such that conductive strip 38 at end 43 of sensor 130 was under a needle, specifically part number PUN-W-.028-.750-10-.005, available from Small Precision Tools of Petaluma, Calif. (12 micron tip radius). The needle was mounted on a weighted ball slide, having a down force adjustable by adding or removing weight. The other side of the ball slide was fixed to the X-Y-Z positioner. An electric probe was attached to the ball slide assembly, which probe was in contact with the needle and in contact with contact pad 46 of conductive strip 38. The X-Y-Z positioning table was heated so as to heat sensor 130 to approximately 65° C. to soften polymer dielectric 40. The needle was then lowered so as to puncture polymer dielectric 40 until the needle contacted conductive strip 38, closing an electrical circuit, at which point the needle was immediately withdrawn. The electrical circuitry was controlled by computer software, easily programmable by one of ordinary skill in the art. According to the method of Example 4, a hole or opening 56 having a diameter of 0.050 mm, defining an electrode 38 having an area of $2 \times 10^{-3}$ mm$^2$ was produced.

EXAMPLE 5

Referring now specifically to FIGS. 2 and 4, onto a partial assembly of each of the sensors fabricated in accordance with Examples 1 and 2, a sensor 130 was fabricated in accordance with Example 3, with the exception that dielectric 40 was deposited so as to completely cover conductive strip 38 in the sensor region at end 43 of sensor 30, and a dielectric material selected so as to substantially absorb radiation emitted from a Xenon laser was utilized. Specifically, a dielectric material available as part number 9615 from DuPont was silk-screened and fired in accordance with Example 3. Subsequently, a Xenon laser was fired at dielectric 40 to create a small hole or opening 56 above conductive strip 38, the hole or opening penetrating through dielectric 40 to expose a small area of conductive strip 38, and defining working electrode 54. Hole 45 was formed between the exposed areas of conductive strips 34 and 36 defining reference and counter electrodes 50 and 52 respectively. A suitable laser is available as model number MEL-31 from Florod Corporation of Gardena, Calif. The exposed area of conductive strip 38, defined by hole or opening 56, and defining working electrode 54, was approximately circular with a diameter of approximately 2 mm.

EXAMPLES 6–8

Deposited atop the sensor region of sensors 30 and 130 fabricated in accordance with Examples 3, 4, and 5, respectively, was solid electrolyte 58. That is, Example 6 comprises a sensor fabricated in accordance with Example 3 and including a solid electrolyte, Example 7 comprises a sensor fabricated in accordance with Example 4 and including a solid electrolyte, and Example 8 comprises a sensor fabricated in accordance with Example 5 and including a solid electrolyte.

In each case, the electrolyte was deposited as lithium-exchanged Nafion, prepared from material available as Catalog Number 27,470-4 from Aldrich Chemical Company, by first neutralizing a 5% solid Nafion solution in a combination of isopropanol (10%), available as Catalog No. 27,470-4 from Aldrich, with lithium hydroxide to a pH of 7 and then concentrating the solution under vacuum to a concentration of about 13.5% solids by weight. This solution was then spun-cast on the sensor assembly to give a film thickness of about 0.007 mm. During spin-casting, the contact pads were masked with tape. The lithium-exchanged Nafion electrolyte film was then cured at 100° C. The film was deposited so as to contact reference, counter, and working electrodes 50, 52 and 54 or 154, respectively, without contacting other sensor components outside of the dielectric layer region.

EXAMPLES 9–14

Membrane materials were formulated from polyvinyl chloride (PVC) and diundecylphthalate (DUP), by dissolving very high molecular weight PVC, available as Catalog No. 34676-4 from Aldrich Chemical Company and having an inherent viscosity of 1.02, and DUP, available as Catalog No. P-129 from Scientific Polymer Products, of Ontario, N.Y. in tetrahydrofuran (THF) as approximately 15% solids by weight, and spin-casting the solution at approximately 1385 revolutions per minute for ten seconds onto a surface. The THF solvent carrier was then evaporated from the membrane by placing the sensor assembly in an oven at 60° C. for two hours. Six membranes were made by this method with the weight percent of PVC in each example, based on the weight of the entire membrane material, as follows:

Example 9, 33%; Example 10, 50%; Example 11, 67%; Example 12 73%; Example 13, 80%; Example 14, 83%.

Figure 6:
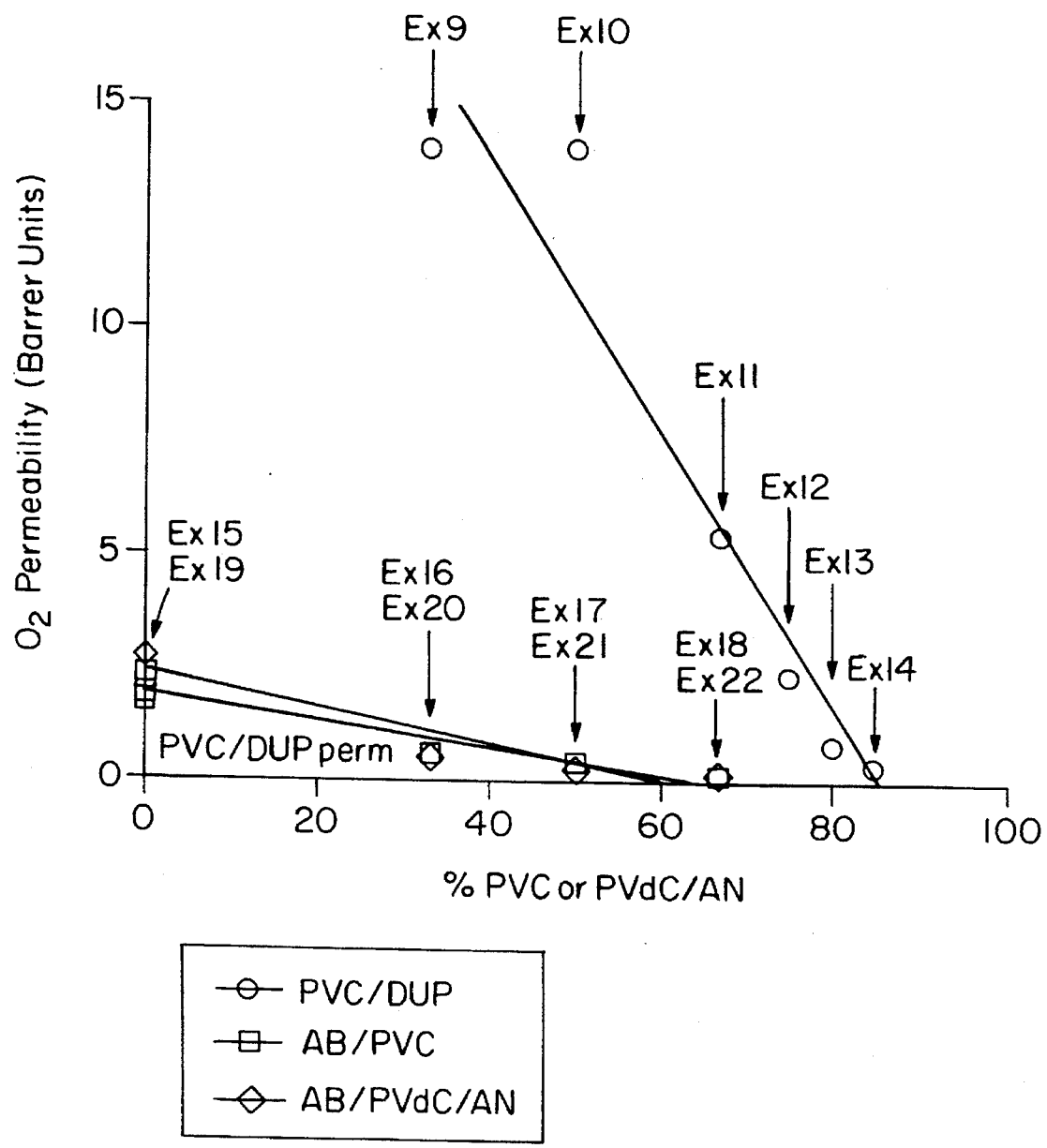
FIG. 6 is a graph of membrane permeability as a function of percent polyvinyl chloride or poly(vinylidene chloride-co-acrylonitrile), according to selected embodiments of the present invention.

The PVC/DUP membranes formulated in accordance with Examples 9–14 were examined to determine their permeability values. The results are plotted in FIG. 6, in which a plot of permeability as a function of percent PVC by weight of the polymer is displayed. The results indicate that at low values of percent DUP by weight, good membrane permeability values are realized but, as the percent by weight of DUP increases, permeability rapidly increased to non-optimum levels. Permeability of from 0.5 to 2.5 Barrer units are preferred for use.

EXAMPLES 15–18

Membranes were formulated in accordance with the reaction method of Examples 9–14 from mixtures of an acrylonitrile-butadiene (AB) copolymer, available as Part No.

533 from Scientific Polymer Products of Ontario, New York, and PVC as in Examples 9–14. Four AB/PVC membranes were made by this method with the weight percent of PVC in each example, based on the weight of the entire membrane material, as follows: Example 15, 0%; Example 16, 33%; Example 17, 50%; Example 18, 67%.

Membranes formulated in accordance with Examples 15–18 were tested to determine their oxygen permeability characteristics, as in Examples 9–14. Results are plotted in FIG. 6. It is notable that a wide range of AB/PVC copolymer mixtures may be formulated within an optimum permeability range. Thus, the blend may be formulated so as to satisfy both oxygen permeability requirements and other physical and chemical requirements.

EXAMPLES 19–22

Membranes were formulated in accordance with the reaction method of Examples 9–14 from a blend of the AB copolymer of Examples 15–18, and poly(vinylidene chloride-co-acrylonitrile) (PVdC/AN), available as catalog no. 396 from Scientific Polymer Products, having a molecular weight of 26,000. Four AB/PVdC/AN membranes were made by this method with the weight percent of PVdC/AN in these Examples, based on the weight of the entire membrane material, as follows: Example 19, 0%; Example 20, 33%; Example 21, 50%; Example 21, 67%.

Membranes formulated in accordance with Examples 19–22 were tested to determine their permeability characteristics as a function of percent PVdC/AN by weight. Results are plotted in FIG. 6. Advantageous results, as noted above with respect to Examples 15–18, are realized.

EXAMPLES 23–46

A series of polyacrylate membranes were formulated. The percent by weight of each component present, based on the weight of the overall membrane, is given for Examples 23–46 in Table 1.

A detailed description of the method of formulation of the composition of Example 46 is given below.

9.46 g acrylonitrile having a molecular weight of 53.06, 19.71 g 2-ethylhexylacrylate having a molecular weight of 184.28, 28.56 g methylmethacrylate having a molecular weight of 100.00, 12.27 g vinyl acetate having a molecular weight of 86.09 and 0.070 g azo-bis-isobutyronitrile as an initiator having a molecular weight of 192.30 were dissolved to form a homogeneous solution. The starting materials were all either freshly distilled or recrystallized. Two glass plates were mounted so as to be parallel to each other, separated by a space of 2 mm. The plates were sealed using a rubber gasket along three edges, and the resultant form was filled with approximately 32 g of the above solution. The glass plate form was then heated to 60° C. for 42 hours in a nitrogen-flushed dry box. The mixture of monomers was polymerized to a solid state. The solid polymer was then dissolved in about 150 ml of chloroform, filtered through a glass filter, and precipitated into four liters of methanol. The white precipitate was then dried in vacuo at 40° C. for three days.

The membranes of Examples 23–45 having the components in the proportions given in Table 1 were formulated and obtained as described with respect to Example 46.

EXAMPLE 47

The following components, in the following amounts, were uniformly admixed and used in the fabrication of a gasket 66: A copolymer of an epichlorohydrin homopolymer and allyl glycidyl ether, available under the trademark Grechon 1100 from Zeon Chemicals, 100 parts by weight; potassium stearate, 4 parts by weight; calcium oxide, 1 part by weight; stearic acid, 1 part by weight; 2-ethyl-2-(hydroxymethyl)-1,3-propanediol trimethacrylate, sold as catalog number SR-350 by Sartomer Co. of West Chester, Pa., 3 parts by weight; and 2,5-bis(t-butylperoxy)-2,5-dimethylhexane, sold under the mark Varox DBPH-50, by R. T. Vanderbilt Co., Inc., 2 parts by weight.

A steel mold having a nickel-filled teflon coating available from Dav-Tech Plating, Inc., was employed. The gasket components were milled to form a ⅜% inch sheet and introduced into a mold having dimensions as described above with respect to preferred sensor embodiments. The components were molded for 20 minutes at 170° C. under a mold force of 9000 lbs. After molding, the mold was cooled via tap water and the gasket was removed.

EXAMPLE 48

A sensor 130 in accordance with Examples 1, 5, and 8 was fabricated, with the following exceptions. Conductive strip 34 was fabricated from silver paste available as part no. 6160 Ag from DuPont. Conductive strip 38 was fabricated from a gold material available as part no. JM6990 from Johnson-Matthey present in an amount of 95% by weight, and a glass bonding frit available as part number PC10129 from Metech, present in an amount of 5% by weight. After deposition of dielectric 40, the portion of conductive strip 34 defining reference electrode 50 was electrochloridized to produce a silver/silver chloride reference. Atop the electrolyte, lithium-exchanged Nafion was deposited on the sensor assembly to give a film thickness of about 0.010 mm. Thereover, membrane 60 was deposited as an acrylonitrile-butadiene copolymer, available as part no. 533 from Scientific Polymer Products. Subsequently, a conventional sample chamber was constructed above the sensor area using a conventional gasket and a clear plastic cover. The sensor was connected to a potentiostat and the working and reference electrodes were biased at a potential difference of approximately −0.900 volts. Wetup to activate the Nafion electrolyte was effected by introducing a saline solution into the conventional sample chamber. Specifically, a wash solution comprising 96.00 mM Nacl, 4.00 mM KCl, 1.25 mM Ca(OAc)$_2$, 16.00 mM LiOAc, 44.00 mM NaOAc, a small amount of a microbicide, and a small amount of a surfactant was introduced. Wetup rate was tested by comparing the current flowing between the working and counter electrodes at 15 minutes following introduction of the saline solution and then at 60 minutes following introduction. It was determined that the electrolyte was actuated to 99% at the 15 minute point.

Subsequently, a series of aqueous oxygen calibrator solutions were applied to the sensor area by introducing them into the sample chamber. Specifically, calibrator solutions carrying oxygen contents of 0%, 12%, and 20% were successively introduced. Percent oxygen content values are given based on total gas dissolved in solution. Calibrator solutions are commonly commercially available.

Figure 7:
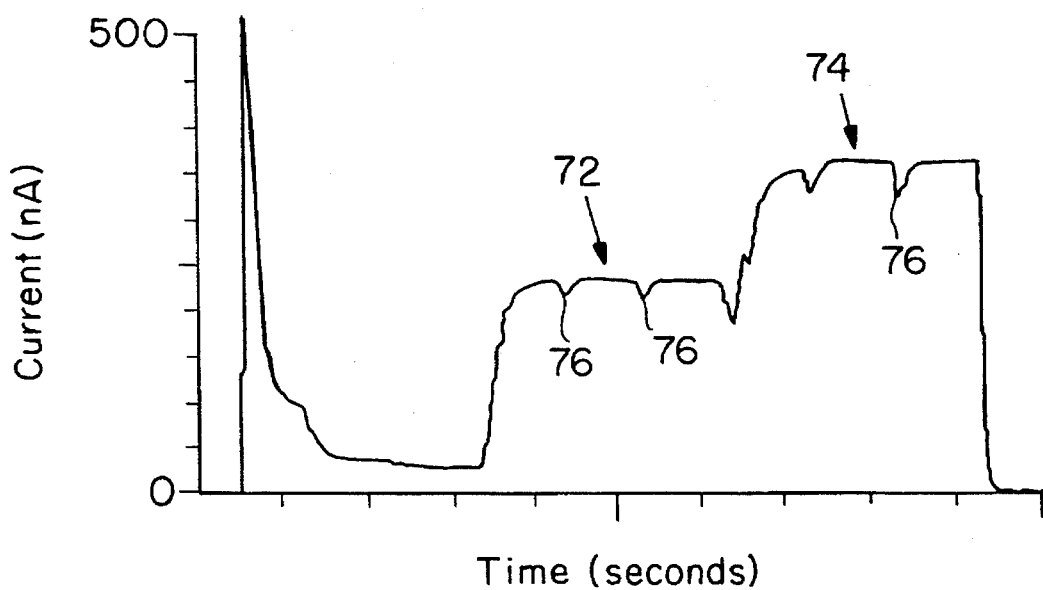
FIG. 7 is a graph of current vs. time illustrating the current response to $pO_2$ in aqueous calibrators, measured according to one embodiment of the invention.

FIG. 7 shows the results of introduction of the aqueous oxygen calibrators, illustrated as a curve of current response versus time. The significant result obtained using the sensor fabricated in accordance with the example is the stable, linear current response at locations 72 and 74 of FIG. 7, representing 12% and 20% oxygen samples, respectively.

This stable, linear response demonstrates the non-depleting nature of working electrode 154, fabricated in accordance with the embodiment illustrated in FIGS. 2 and 4 using the laser hole or opening formation method. Thus, a combination of a small, laser-hole-formed working electrode with a cover membrane selected so as to advantageously pass oxygen in limited quantities but pass water vapor very rapidly, with a solid electrolyte therebetween, results in a cumulative non-depleting sensor fabricated conveniently and economically. Inconsistencies 76 in FIG. 7 represent current anomalies resulting from serial manual sample introduction of a plurality of calibration samples.

EXAMPLE 49

Figure 8:
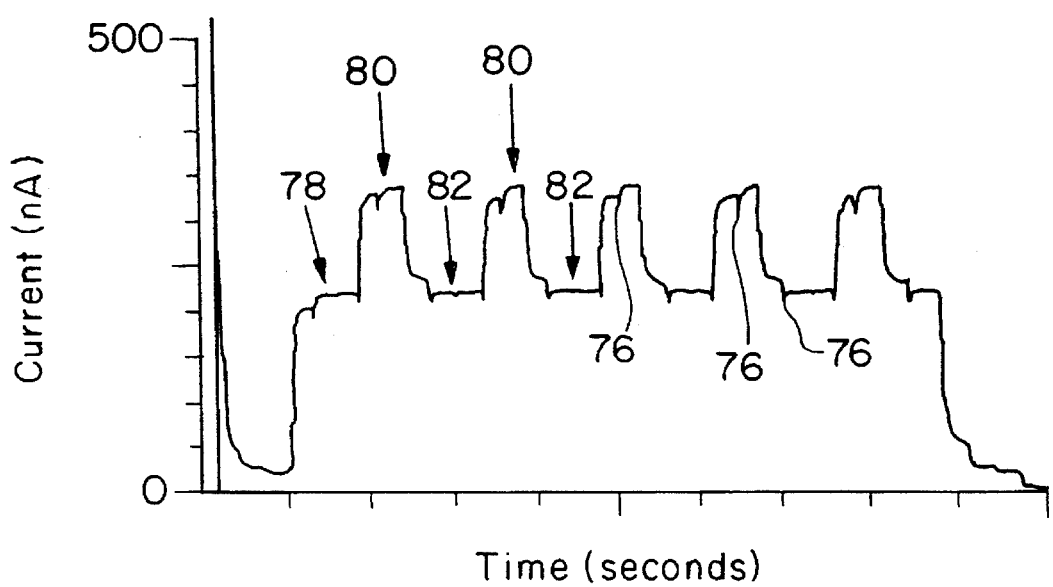
FIG. 8 is a graph of current vs. time illustrating the current response to $pO_2$ in blood samples, measured according to one embodiment of the present invention.

Blood samples having predetermined $pO_2s$ were introduced into the conventional sample chamber of the sensor of Example 48, and the sensor was polarized as in Example 47, following wetup and calibration. Specifically, tonometered blood samples carrying 12% oxygen and 20% oxygen, respectively, were introduced into the conventional sample chamber. FIG. 8 graphically illustrates current response versus time in this experiment. Location 78 of the curve represents application of a 12% aqueous oxygen calibrator solution, locations 80 represent current response upon application of the 20% oxygen blood samples, and locations 82 represent application of the 12% oxygen blood samples. Significantly, as noted above with respect to the calibration experiment illustrated in FIG. 7, the data illustrated in FIG. 8 shows the non-depleting nature of the sensor fabricated in accordance with one embodiment of the present invention, illustrated in that locations 80 and 82 show rapid, smooth, and repeatable equilibration of current response to oxygen content in the blood. As in FIG. 7, in FIG. 8 anomalies 76 represent serial introduction of samples into the sensor.

EXAMPLES 50–54

Figure 9:
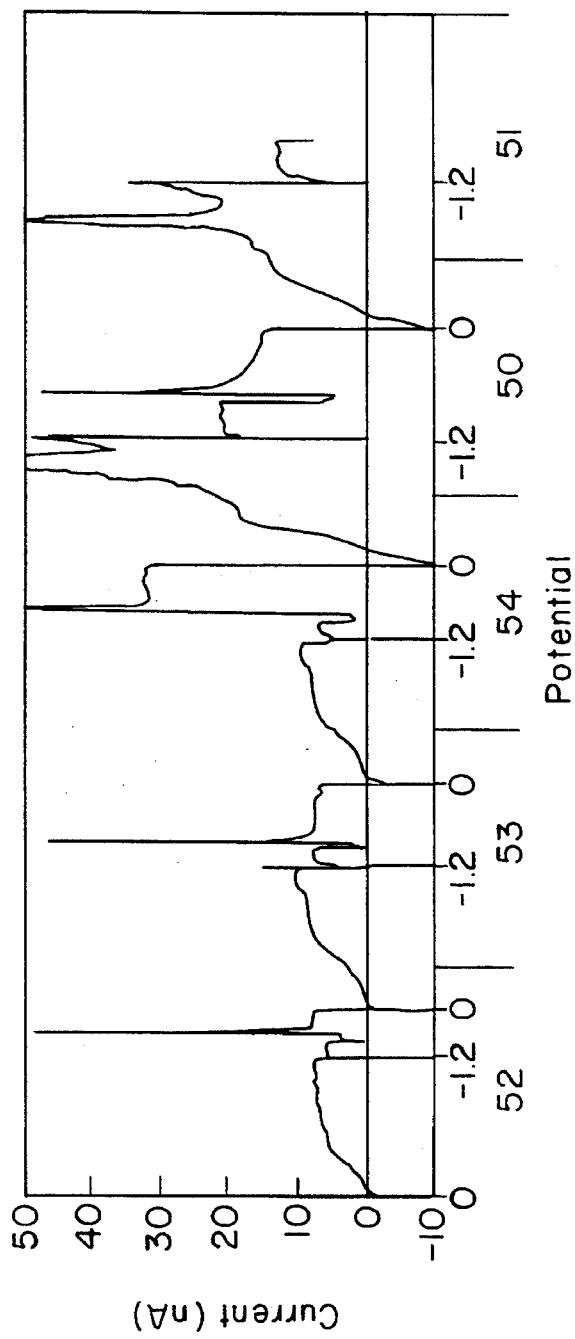
FIG. 9 illustrates linear sweep voltamograms, after 16 days use, of sensors fabricated according to three embodiments of the present invention.
Figure 11:
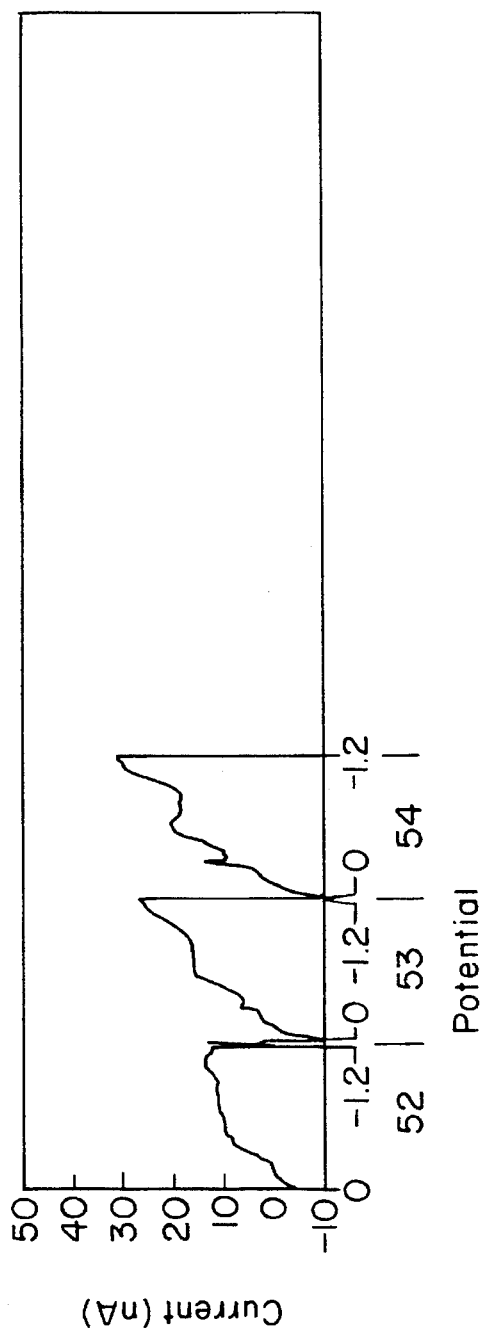
FIG. 11 illustrates linear sweep voltamograms, after 60 days use, of sensors fabricated according to three embodiments of the present invention.
Figure 10:
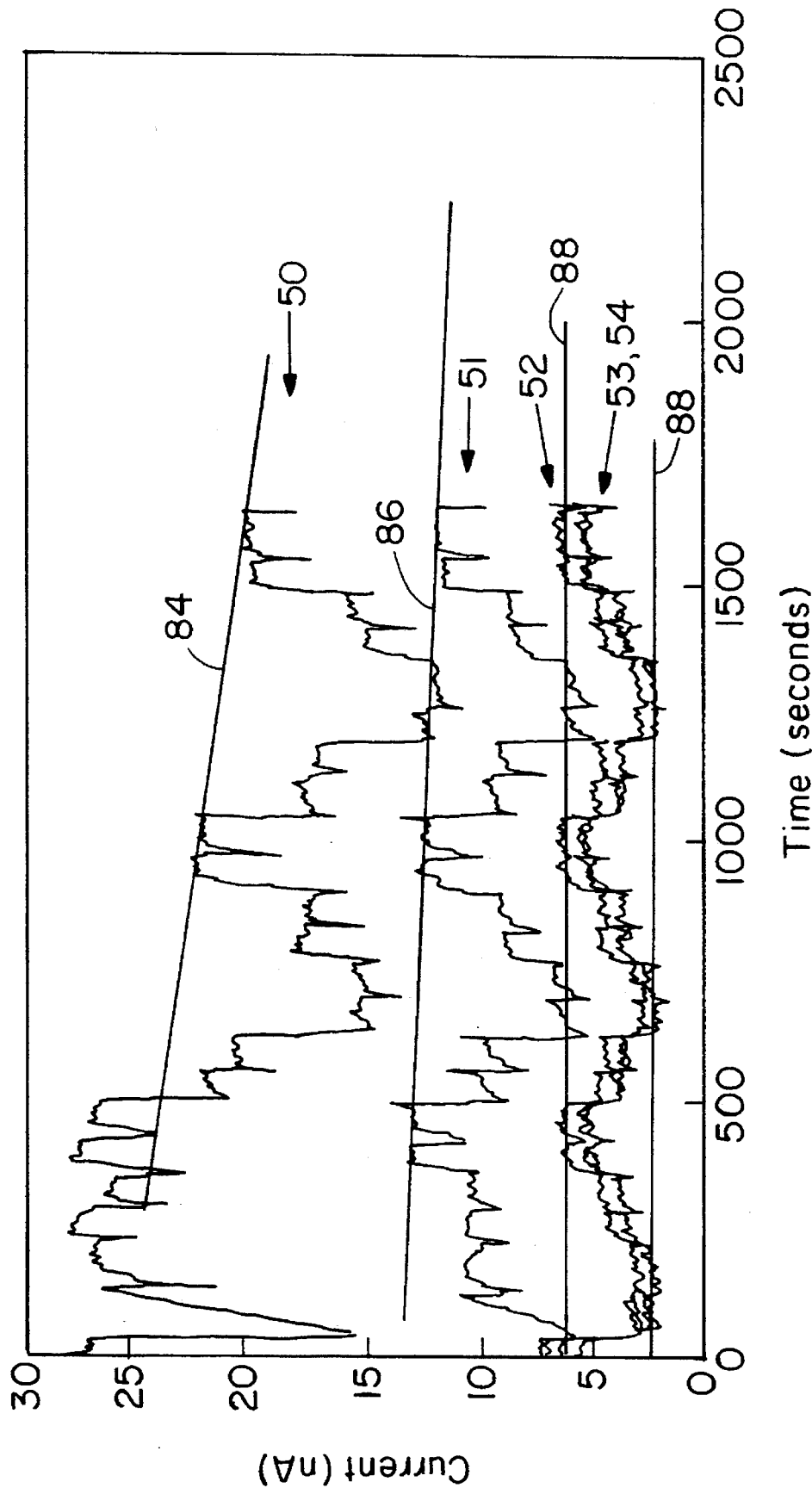
FIG. 10 illustrates sensor response to aqueous oxygen calibrator solutions, after 16 days use, of sensors fabricated according to three embodiments of the present invention.
Figure 12A:
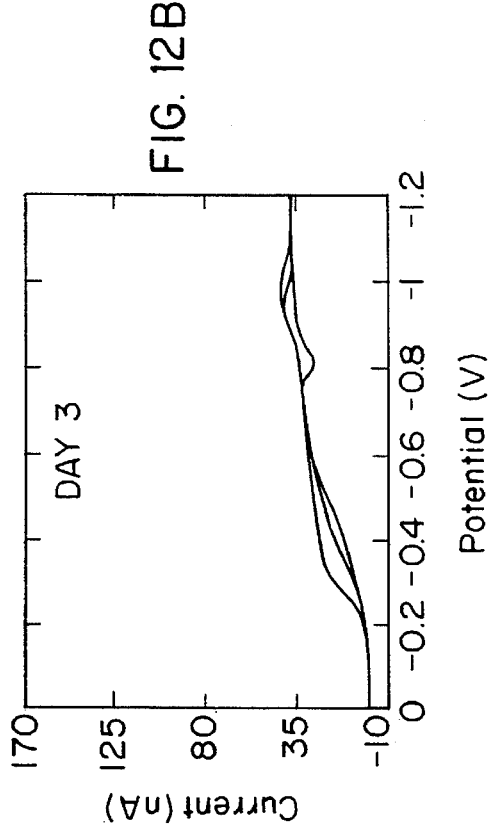
FIGS. 12A–12G illustrate cyclic voltamograms, taken after various periods of use, of a sensor fabricated according to one embodiment of the present invention.
Figure 12B:
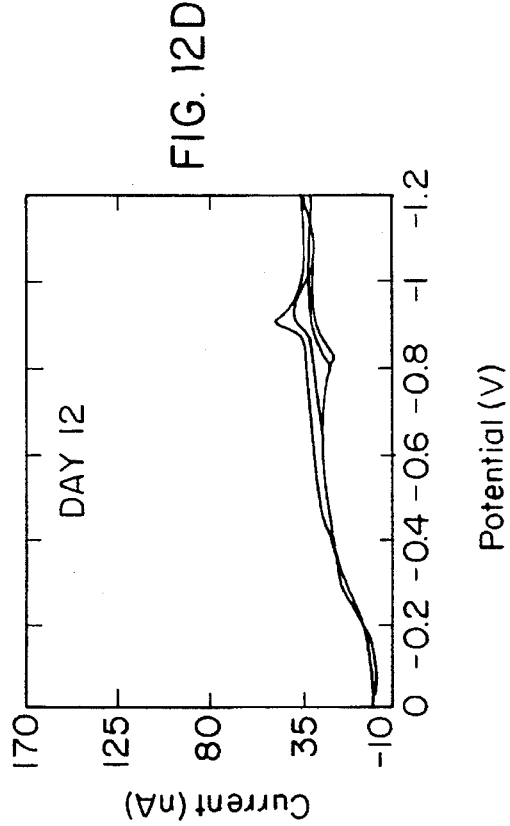
Figure 12C:
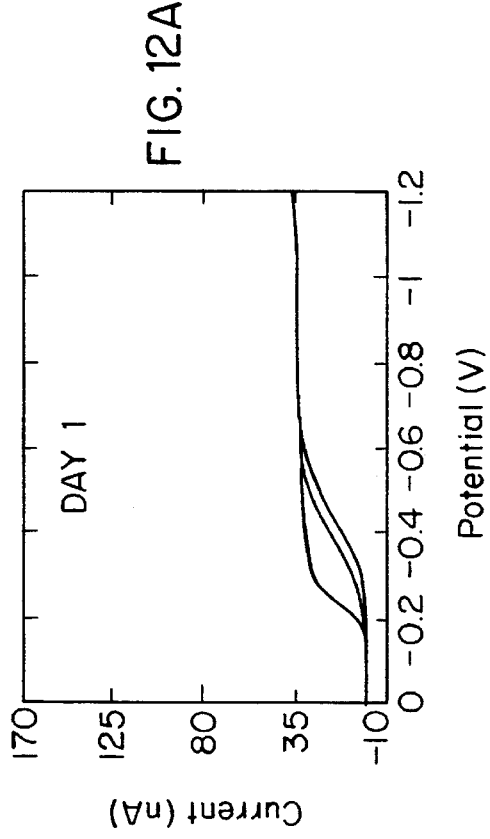
Figure 12D:
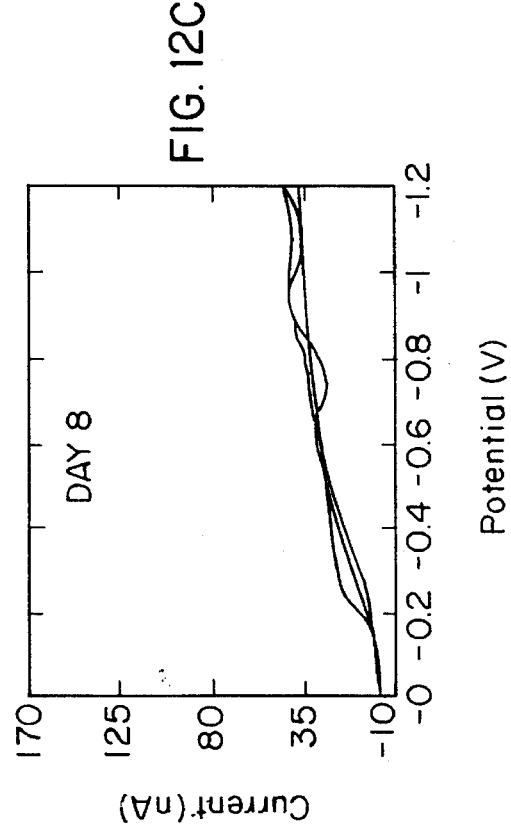
Figure 12E:
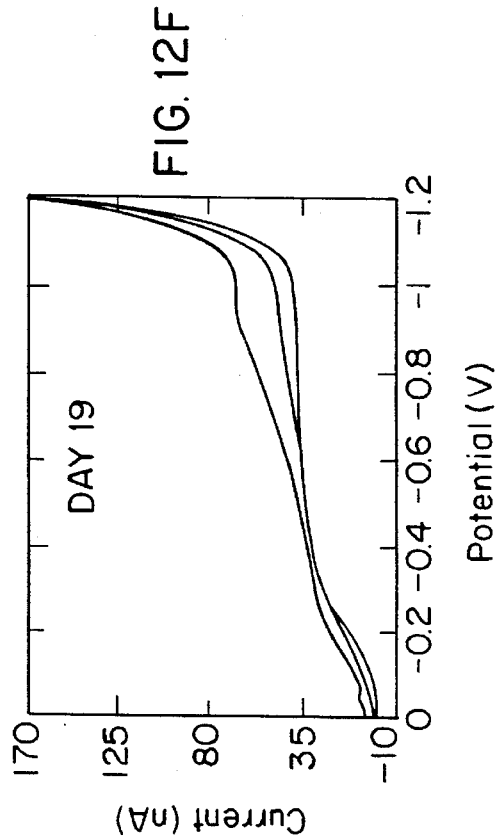
Figure 12F:
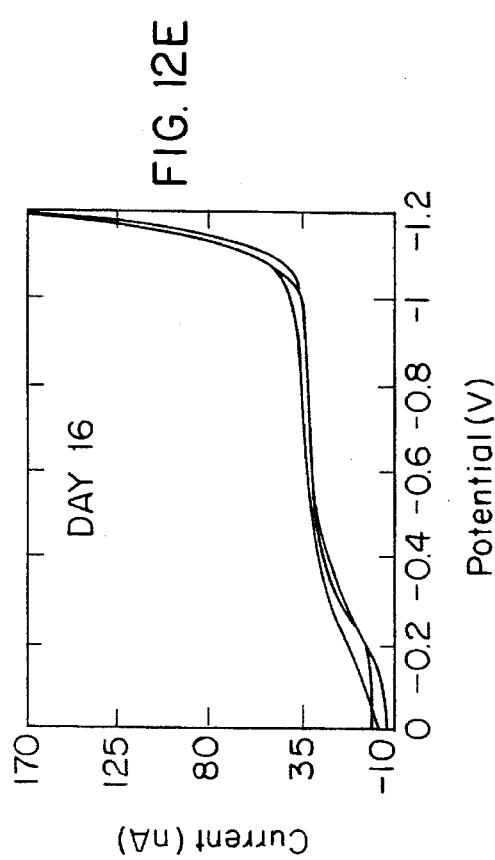
Figure 12G:
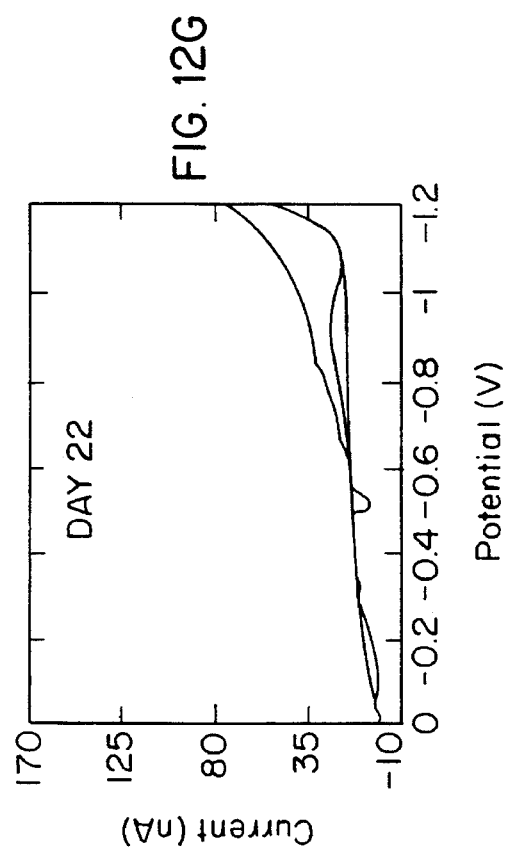
Figure 13A:
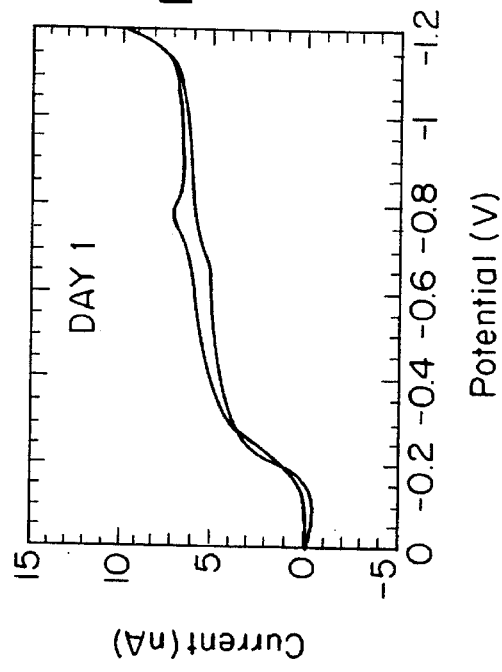
Figure 13B:
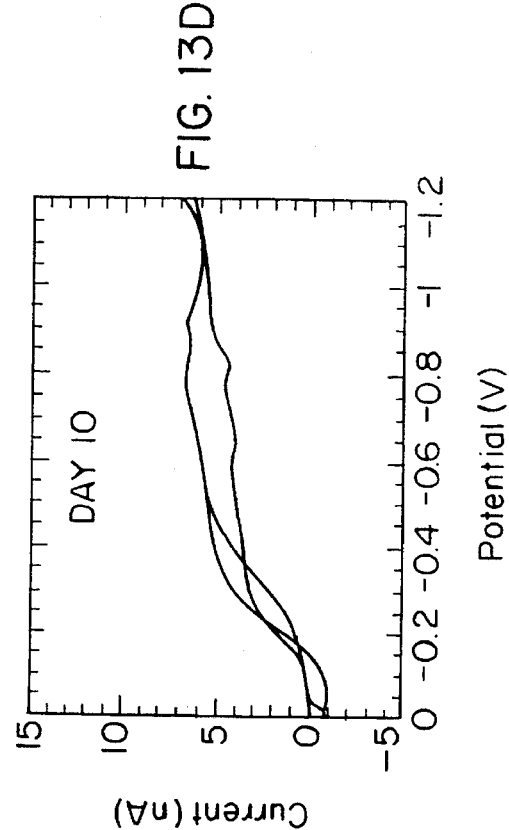
Figure 13C:
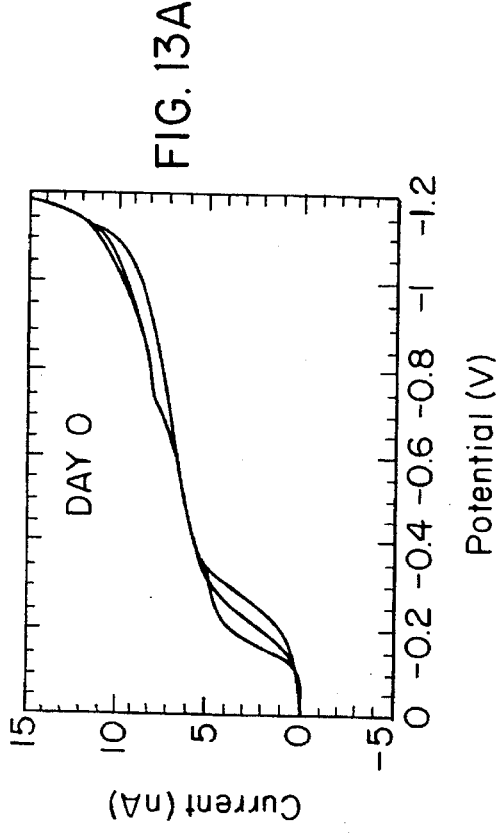
Figure 13D:
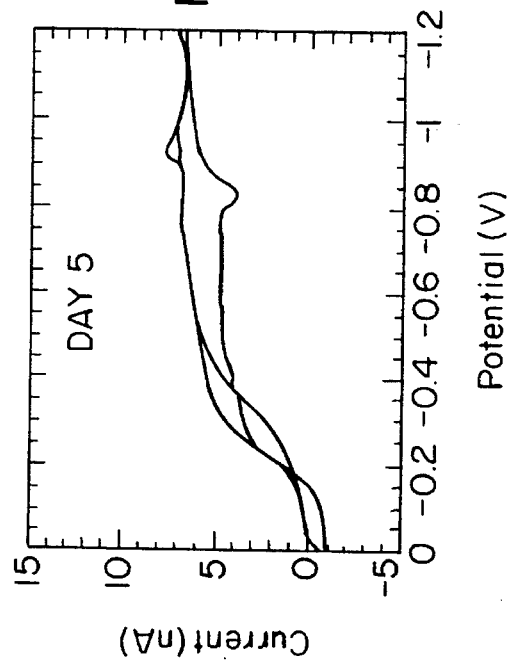
Figure 14A:
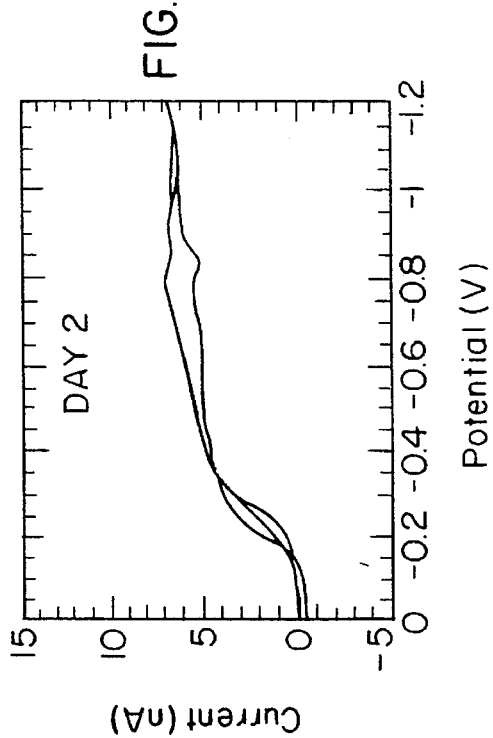
FIGS. 14A–14H illustrate cyclic voltamograms, taken after various periods of use, of a sensor fabricated according to one embodiment of the present invention.
Figure 14B:
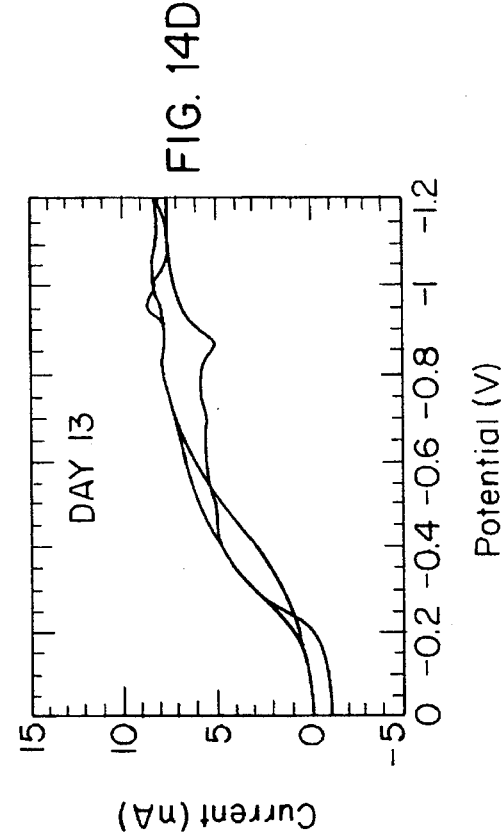
Figure 14C:
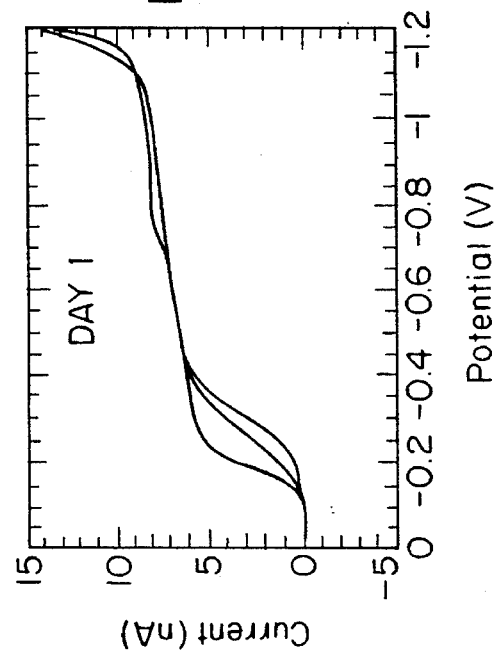
Figure 14D:
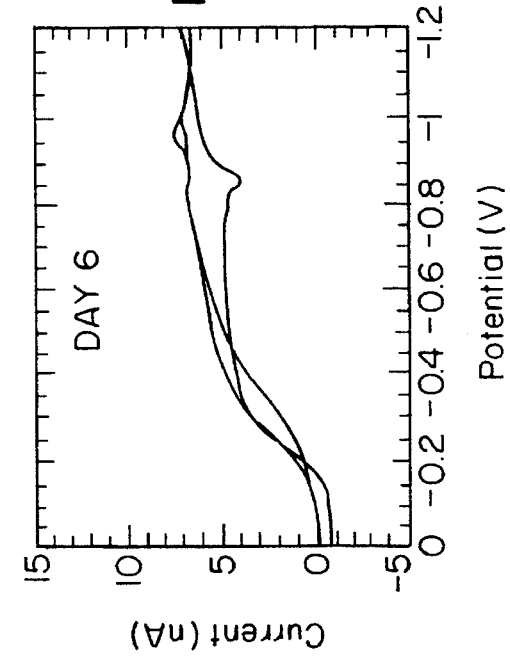
Figure 14E:
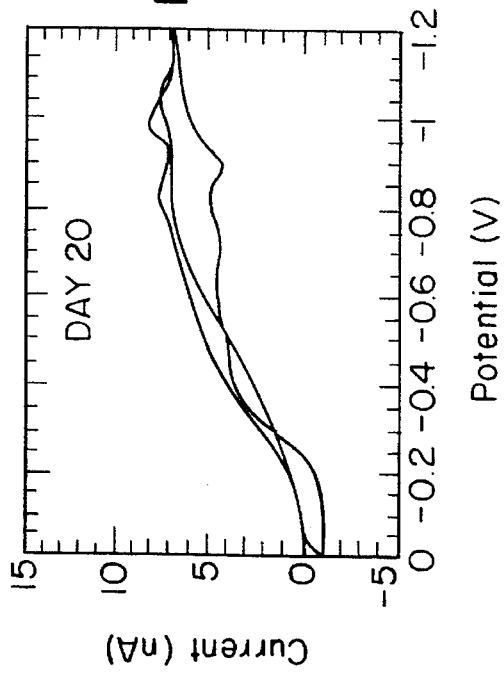
Figure 14F:
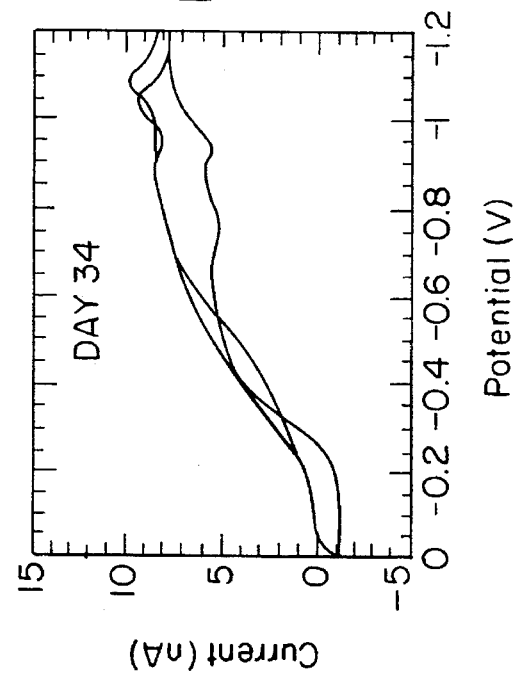
Figure 14G:
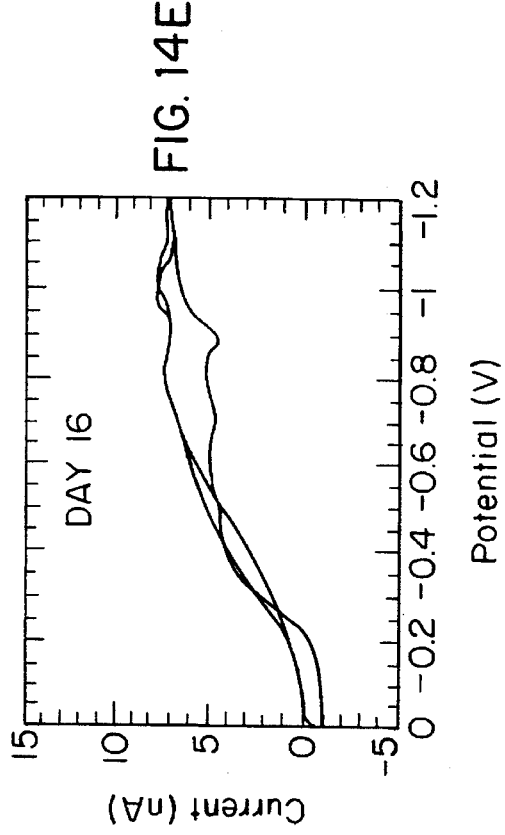
Figure 14H:
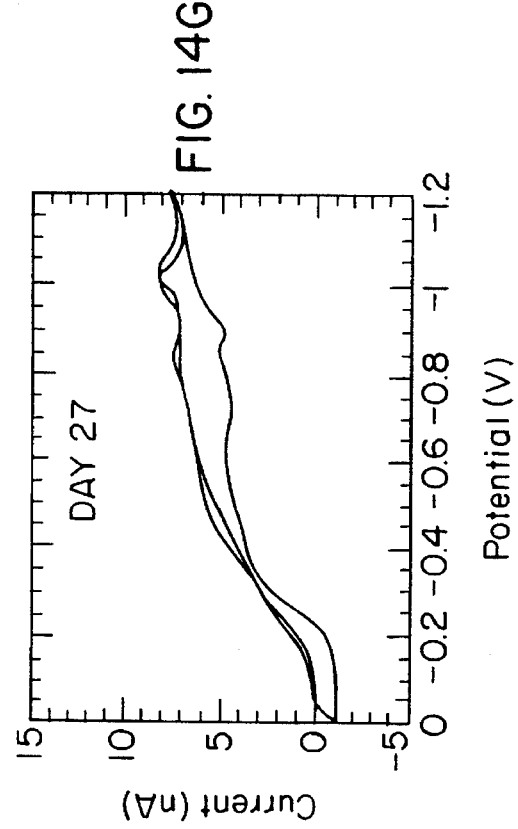

In these and following examples, the advantageous longevity of several preferred embodiments of the present invention will be demonstrated. Sensors were fabricated as follows: Examples 50 and 51, according to Examples 2, 3, 6, and 16; Example 52, according to Examples 2, 3, 6, and 45; Examples 53 and 54, according to Examples 2, 3, 6, and 46. Subsequently, a sample chamber having a volume of approximately 1.5 µl was constructed above the sensor area using a gasket in accordance with Example 47 and a cover member as described above. Each sensor was attached to a potentiostat, set at a potential of −0.800 V between the working and reference electrodes, and the sample chambers were filled with the wash solution described above. Daily, each was flushed with 0.1M aqueous NaCl and a linear sweep voltamogram (LSV) from 0 to −1.200 V of each sensor was obtained, then each was flushed with the wash solution and again stored at −0.800 V potential. FIG. 9 graphically illustrates LSV's from 0 to 1.2 V obtained on day 16 of the experiment, plotted as current response as a function of applied potential. The LSV's of Examples 52, 53, and 54 appear remarkably good in their smooth current response that is substantially free of impurity and other spurious peaks, while those of Examples 50 and 51 display significant spurious peaks. FIG. 10 illustrates response of these sensors to oxygen calibrator samples as described in Example 48, plotted as current response as a function of $pO_2$. Included are plots 84, 86, and 88 of the linearity of current response as a function of repeated calibrator application. The sensors of Examples 52, 53, and 54 show remarkable linearity, and even the sensor of Example 51 shows relatively good linearity given its LSV illustrated in FIG. 9, demonstrating that satisfactory performance may be obtained despite moderate impurity peaks in voltamograms. FIG. 11 illustrates LSV's obtained on day 60 of the sensors of Examples 52, 53, and 54, showing extremely good stability of the sensors over time, evidenced by the lack of significant impurity and other spurious peaks.

EXAMPLES 55–57

In Examples 55–57, sensors were fabricated as follows: Example 55, according to Examples 2, 3, 6, and 42; Example 56, according to Examples 2, 3, 6, and 45; Example 57, according to Examples 2, 3, 6, and 46. Subsequently, a sample chamber having a volume of approximately 1.5 ul was constructed above the sensor area using a gasket in accordance with Example 47 and a cover member as described above. Each sensor was attached to a potentiostat, set at a potential of −0.800 V between the working and reference electrodes, and the sample chambers were filled with the wash solution described above. Daily, each was flushed with a fresh wash solution, and a ⅔ cyclic voltamogram (CV) between 0 and −1.200 V of each sensor was obtained. Each ⅔ cyclic voltamogram was carried out by polarizing the sensor at 0 V vs. Ag/AgCl, sweeping the voltage to −1.200 V, sweeping back to 0 V, and sweeping finally back to −1.200 V, monitoring and plotting current response as a function of applied voltage along the way. Then each was flushed with the wash solution and again stored at −0.800 V potential.

The results of these experiment on various days for Examples 55, 56, and 57 are illustrated in FIGS. 12A–G, 13A–13G, and 14A–14H, respectively. Excellent stability is demonstrated, as the ⅔ cyclic voltamograms do not change appreciably in appearance from one day's experiment to another's. Indeed, all the ⅔ cyclic voltamograms show absence of substantial impurity or other spurious peaks.

EXAMPLE 58

A sensor 30 was fabricated in accordance with Examples, 2, 3, and 6, with a membrane fabricated in accordance with Example 24 deposited thereover, with the following exceptions. Two layers of dielectric were deposited, and the Nafion electrolyte was deposited in a thickness of 10 µm. Subsequently, a sample chamber having a volume of approximately 1.5 µl was constructed above the sensor using a gasket in accordance with Example 47 and a cover membrane as described above.

The sensor was subjected to five days of electrochemical testing, using aqueous oxygen calibrator solutions, human whole blood, and human serum. Specifically, a feasibility study was carried out in which the sensor was set at a predetermined potential, and data was collected on 30 whole blood human samples at three different levels of oxygen for three days in a row. The blood samples were collected and tonometered at 37° C. to one of three predetermined oxygen concentration levels. Data was not collected from serum samples introduced into the sample chamber, but serum was introduced so as to subject the sensor to more human samples. Serum was run at ambient temperature and gas levels. Between each human blood sample, human serum sample, and between each calibrator level introduction, the wash solution of Example 48 was introduced into the sample chamber. During the testing, the sensor was connected to a potentiostat and the working and reference electrodes were biased at a potential difference of approximately −0.800 volts. Data points were collected every two seconds.

On day 1, wetup was effected by introducing the wash solution into the sample chamber. Then, a 32-minute calibration curve was obtained by introducing a sample of a 5.99% oxygen calibrator into the sample chamber, followed by a 60-second data collection period, after which the step was repeated. A 12.94% oxygen calibrator was then sampled identically, followed by a 23.99% oxygen level calibrator, sampled identically.

On each of days 2–4, the following protocol was carried out. First a calibration step as described above with regard to the day 1 data acquisition was carried out. Then, a 50-minute protocol was carried out by introducing the wash solution into the sample chamber, followed by a two-minute data collection period, followed by introduction of human serum at ambient oxygen concentration, followed by a two-minute data collection period. The wash/serum sequence was repeated ten times, ending with a wash step. The entire serum protocol was repeated for a total of 20 serum samples. Following the serum protocol, the above-described calibration protocol was run. Then a 47-minute human whole blood protocol was run. Specifically, a 5.99% oxygen calibrator was introduced into the sample chamber, followed by a one-minute data collection period. This sequence was repeated with a 12.94% oxygen calibrator, and then with a 23.99% oxygen calibrator. Subsequently, the wash solution was introduced into the sample chamber and a 90-second data collection was carried out. Then a sample of whole blood tonometered to 21% oxygen was introduced into the sample chamber, followed by a 60-second data collection period, followed by introduction of the wash solution, followed by introduction of the tonometered whole blood sample. The sequence was repeated until 10 whole blood samples had been introduced. The above-noted calibration protocol was then run. Then the whole blood protocol was repeated, first with a 12.94% oxygen tonometered whole blood sample, and then with a 7% oxygen tonometered whole blood sample. At the end of this protocol, the calibration protocol was repeated.

On day 5, the above-noted calibration protocol was repeated. Then, the sensor was evaluated by obtaining a sensor polarogram as described above with respect to Examples 55–57, with the exception that ½ of a cyclic voltamogram was run. The polarogram was run from 0 to −1.200 volts.

Figure 15:
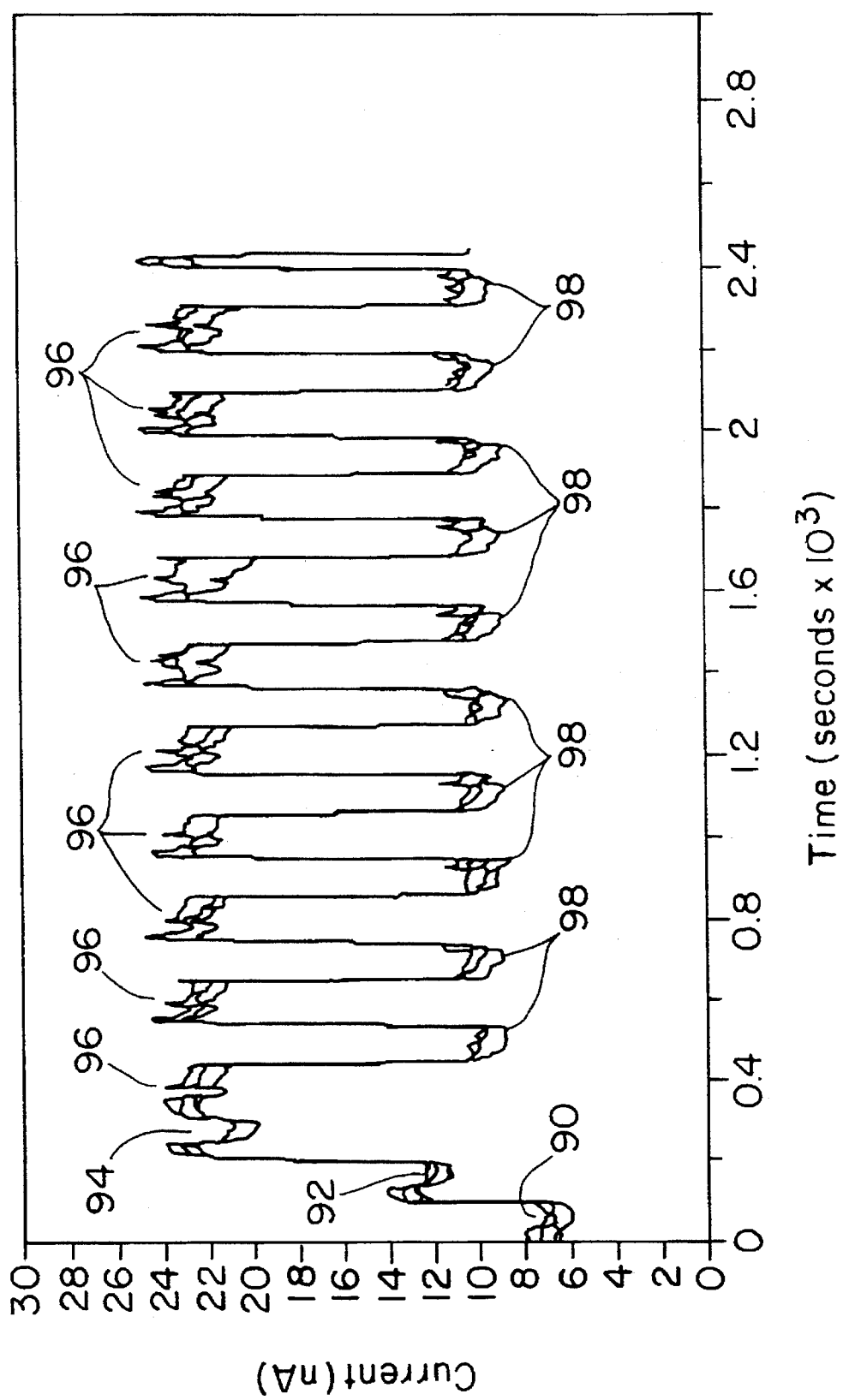
FIG. 15 illustrates sensor response to aqueous oxygen calibrator solutions and to tonometered whole human blood samples according to one embodiment of the present invention.

FIG. 15 illustrates results of the human whole blood tonometered samples exposed to the sensor as described above. The data was collected on day 2 of the test. Introduction of the 5.99% oxygen calibrator is represented at 90, introduction of the 12.94% oxygen calibrator is represented at 92, and introduction of the 23.99% oxygen calibrator is represented at 94. Introduction of the wash solution is represented at 94. Introduction of the wash solution is represented at locations 96. Introduction of the whole blood samples tonometered to 12.94% oxygen are represented by locations 98. The discrepancy between locations 98, representing 12.94% oxygen tonometered whole blood, and locations 92, representing 12.94% oxygen calibrator, is due to the well-known characteristic of blood in producing lower oxygen readings than calibrator solutions. Adjustment for such discrepancy is easily made by those of ordinary skill in the art. Significant results illustrated in FIG. 15 include the good precision in current response to oxygen levels, and good linearity in the calibration step observed.

Figure 16:
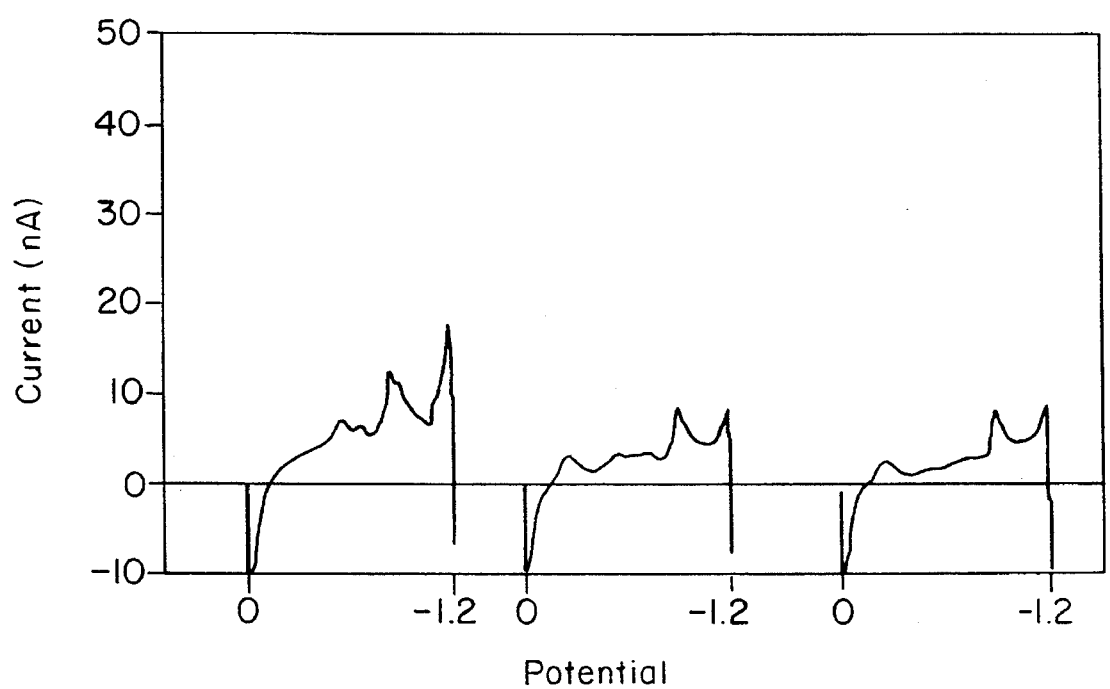
FIG. 16 illustrates polarograms, taken after five days of sensor testing using oxygen calibrator solutions, human serum, and tonometered human whole blood samples, according to one embodiment of the present invention.

FIG. 16 illustrates three representative polarograms obtained on day 5 of the test, illustrating good durability of the sensor.

The preceding examples are set forth to illustrate specific embodiments of the invention and are not intended to limit the scope of the invention. Additional embodiments and advantages within the scope of the claimed invention, for example measuring electroactive species other than oxygen with sensing means described herein, and employing components of the inventive sensor for purposes other than electrochemical analysis, will be apparent to those of ordinary skill in the art.

TABLE 1

| Ex. No. | 1 | 2 | 3 | 4 | 5 | 6 | 7 | 8 | 9 |
|---|---|---|---|---|---|---|---|---|---|
| 23 | 72.8 | 50% | 10% | 40% | | | | | |
| 24 | 45.1 | 60% | 20% | 20% | | | | | |
| 25 | 39.5 | 70% | 30% | | | | | | |
| 26 | 21.5 | 60% | 40% | | | | | | |
| 27 | 11.6 | 30% | 50% | 20% | | | | | |
| 28 | 17.4 | 40% | | 20% | 40% | | | | |
| 29 | −3.9 | 40% | 40% | | | 20% | | | |
| 30 | −17.9 | 30% | 30% | | | 40% | | | |
| 31 | −15.6 | 30% | | | 40% | 30% | | | |
| 32 | 18.3 | 60% | | | 30% | 10% | | | |
| 33 | 54.8 | | | 70% | | | | 30% | |
| 34 | 84.9 | | 20% | 80% | | | | | |
| 35 | 47.3 | | 40% | 40% | | | 20% | | |
| 36 | 30.1 | 50% | 40% | | | | | | 10% |
| 37 | 28.1 | 40% | 50% | | | | | | 10% |
| 38 | 15.4 | 30% | 60% | | | | | | 10% |
| 39 | 43.0 | 52% | 35% | | | | | | 13% |
| 40 | 38.7 | 44% | 40% | | | | | | 16% |
| 41 | 29 | 55% | 10% | 10% | 15% | 10% | | | |
| 42 | 18 | 40% | 20% | 20% | 15% | 5% | | | |
| 43 | 32 | 40% | 20% | 30% | | 10% | | | |
| 44 | 34 | 30% | 25% | 40% | | 5% | | | |
| 45 | 59 | 25% | 10% | 40% | | 25% | | | |
| 46 | 42 | 25% | 15% | 40% | | 20% | | | |

1 - Tg (°C.)
2 - Acrylonitrile
3 - 2-ethylhexylmethacrylate
4 - methylmethacrylate
5 - dodecylmethacrylate
6 - vinylacetate
7 - cyclohexylmethacrylate
8 - 2-hydroxypropylmethacrylate
9 - acrylamide

What is claimed is:

1. A method for forming a microelectrode for use as a working electrode in a planar, solid-state sensor or the like, comprising the steps of:

selecting an electrically nonconductive substrate, combining said substrate with an electrically conductive material with said electrically conductive material forming a layer adjacent said electrically nonconductive substrate, coating at least a portion of the electrically conductive material with an electrically insulating material, puncturing the electrically insulating material to form at least one hole or opening therein with a needle in communication with electric circuit means in communication with the electrically conductive material, which moves between a first position and a second position in which the electric circuit means generates a signal;

withdrawing the needle when the signal is generated;

said insulating material being selected to firmly adhere to the conductive material such that when the at least one hole or opening is formed, an exposed, electrically addressable portion of the electrically conductive material is created, defining at least one electrode having a size defined by the cross-sectional area of the hole or opening.

2. A method as recited in claim 1, wherein said puncturing step is carried out by heating elements selected from the group consisting of the substrate, the needle, and both the substrate and the needle, to a set temperature prior to puncturing, and wherein said electrically insulating material is selected to be readily punctured at said set temperature.

3. A method for forming a microelectrode for use as a working electrode in a planar, solid-state sensor or the like, comprising the steps of:

selecting an electrically nonconductive substrate, combining said substrate with an electrically conductive material with said electrically conductive material forming a layer adjacent said electrically nonconductive substrate;

coating a surface of the electrically conductive material with an electrically insulating material selected to firmly adhere to the conductive material;

passing a needle in communication with electric circuit means in communication with the electrically conductive material through the electrically insulating material, which needle is moved between a plurality of positions relative to the surface, some of which positions cause the electric circuit means to generate signals; and withdrawing the needle when a set signal is generated indicating a set relative position.

* * * * *